(12) United States Patent
Schibli et al.

(10) Patent No.: US 10,322,195 B2
(45) Date of Patent: Jun. 18, 2019

(54) $^{18}$F-SACCHARIDE-FOLATES

(75) Inventors: Roger Schibli, Baden (CH); Rudolf Moser, Schaffhausen (CH); Cristina Magdalena Muller, Nussbaumen (CH); Simon Mensah Ametamey, Zurich (CH); Cindy Ramona Fischer, Freising (DE); Viola Groehn, Dachsen (CH)

(73) Assignee: Merck & CIE, Schaffhausen (CH)

( * ) Notice: Subject to any disclaimer, the term of this patent is extended or adjusted under 35 U.S.C. 154(b) by 27 days.

(21) Appl. No.: 14/239,275

(22) PCT Filed: Aug. 21, 2012

(86) PCT No.: PCT/EP2012/066236
§ 371 (c)(1),
(2), (4) Date: Feb. 18, 2014

(87) PCT Pub. No.: WO2013/026842
PCT Pub. Date: Feb. 28, 2013

(65) Prior Publication Data
US 2014/0193337 A1    Jul. 10, 2014

(30) Foreign Application Priority Data

Aug. 22, 2011    (EP) .................................... 11178260

(51) Int. Cl.
| | | |
|---|---|---|
| *A61K 51/00* | (2006.01) | |
| *A61M 36/14* | (2006.01) | |
| *A61K 51/04* | (2006.01) | |
| *C07B 59/00* | (2006.01) | |
| *G01N 33/60* | (2006.01) | |

(52) U.S. Cl.
CPC ........ *A61K 51/0491* (2013.01); *C07B 59/005* (2013.01); *G01N 33/60* (2013.01)

(58) Field of Classification Search
CPC ... A61K 51/0491; G01N 33/60; C07B 59/005

USPC ........................................................ 424/1.73
See application file for complete search history.

(56) References Cited

U.S. PATENT DOCUMENTS

| | | |
|---|---|---|
| 8,344,140 B2 | 1/2013 | Ametamey et al. |
| 2010/0111863 A1 | 5/2010 | Ametamey et al. |

FOREIGN PATENT DOCUMENTS

WO    2008125615 A1    10/2008

OTHER PUBLICATIONS

Bettio et al. J. Nucl. Med. 2006, 47, 1153-1160.*
Maschauer et al. Carbohydrate Res. 2009, 334, 753-761.*
International Search Report from PCT/EP2012/066236 dated Nov. 14, 2012.

* cited by examiner

*Primary Examiner* — Michael G. Hartley
*Assistant Examiner* — Sean R Donohue
(74) *Attorney, Agent, or Firm* — Millen White Zelano and Branigan, PC; Csaba Henter

(57) ABSTRACT

The present invention is directed towards new $^{18}$F-folate radiopharmaceuticals, wherein the $^{18}$F isotope F is linked via a prosthetic group, more specifically via a prosthetic group having a saccharide group, such as a cyclic mono- or oligosaccharide, preferably based on a pyranoside or furanoside, which is covalently linked to the glutamate portion of a folate or derivative thereof, a method of their preparation, as well as their use in diagnosis and monitoring of cancer and inflammatory and autoimmune diseases and therapy thereof.

13 Claims, 8 Drawing Sheets

X = ¹⁸F labelled compound or
¹⁹F(reference compound)

18F-SACCHARIDE-FOLATES

FIELD OF INVENTION

The present invention is directed towards new $^{18}$F-folate radiopharmaceuticals, wherein the $^{18}$F isotope is linked via a prosthetic group, more specifically via a prosthetic group comprising a saccharide group, such as cyclic mono- and oligosaccharides, which is covalently linked to the glutamate portion of a folate or derivative thereof, a method of their preparation, as well as their use in diagnosis and monitoring of cancer and inflammatory and autoimmune diseases and therapy thereof.

BACKGROUND

Cell-specific targeting for delivery of effector moieties such as diagnostic or therapeutic agents is a widely researched field and has led to the development of non-invasive diagnostic and/or therapeutic medical applications. In particular in the field of nuclear medicine procedures and treatments, which employ radioactive materials emitting electromagnetic radiations as γ-rays or photons or particle emitting radiation, selective localization of these radioactive materials in targeted cells or tissues is required to achieve either high signal intensity for visualization of specific tissues, assessing a disease and/or monitoring effects of therapeutic treatments, or high radiation dose, for delivering adequate doses of ionizing radiation to a specified diseased site, without the risk of radiation injury in other e.g. healthy tissues. It is thus of crucial interest to determine and assess cell-specific structures and in particular structures that are present in case of tumors (i.e. cancer) or inflammatory and autoimmune diseases, such as receptors, antigens, haptens and the like which can be specifically targeted by the respective biological vehicles.

The folate receptor (FR) has been identified as one of these structures. The FR is a high-affinity ($K_D < 10^{-9}$ M) membrane-associated protein. In normal tissues and organs FR-expression is highly restricted to only a few organs (e.g. kidney, lungs, choroids plexus, and placenta), where it largely occurs at the luminal surface of epithelial cells and is therefore not supplied with folate in the circulation. The FR-alpha is frequently overexpressed on a wide variety of specific cell types, such as epithelial tumours (e.g. ovarian, cervical, endometrial, breast, colorectal, kidney, lung, nasopharyngeal), whereas the FR-beta is frequently overexpressed in leukaemia cells (approx. % of acute myelogenous leukaemia (AML) are FR-beta positive). Both may therefore be used as a valuable tumour marker for selective tumour-targeting (Elnakat and Ratnam, Adv. Drug Deliv. Rev. 2004; 56:1067-84). In addition, the FR-beta isoform has been found on activated (but not resting) macrophages. Activated macrophages are involved in inflammatory pathologies such as e.g. rheumatoid arthritis, psoriasis, Crohn's disease, ulcerative colitis, systemic lupus erythematosus, atherosclerosis, diabetes, osteoarthritis, glomerulonephritis, infections, etc.

The literature reports several preclinical studies of folate-based imaging agents for detection/localization of sites of inflammation as well as folate receptor targeted therapy of these diseases. Recently, a clinical study has been published that reports the results of imaging studies in patients with rheumatoid arthritis using the FolateScan (Turk et al., Arthritis and Rheumatism 2002, 45, 1947-1955; Paulos et al., Adv. Drug Deliv. Rev. 2004, 56, 1205-1217; Chen et al., Arthritis Research & Therapy 2005, 7, 310-317; Hattori et al., Biol. & Pharm. Bull. 2006, 29, 1516-1520; Chandraseka et al., J. Biomed. Mat. Res. Part A 2007, 82, 92-103; Varghese et al., Mol. Pharmaceutics. 2007, 4, 679-685; Low et al. Discovery and development of folic-acid-based receptor targeting for imaging and therapy of cancer and inflammatory diseases 2008, 41, 120-129; Matteson et al., Clinical and Experimental Rheumatology 2009, 27, 253-259).

Folic acid, which is based on a pteridine skeleton conjugated through a benzoylamino moiety to a glutamate, and its derivatives have thus been intensively studied over the past 15 years as targeting agents for the delivery of therapeutic and/or diagnostic agents to cell populations bearing folate receptors in order to achieve a selective concentration of therapeutic and/or diagnostic agents in such cells relative to normal cells.

Various folic acid derivatives and conjugates are known and have been (pre)clinically evaluated, including folate radiopharmaceuticals (Leamon and Low, Drug Discov. Today 2001; 6:44-51; U.S. Pat. No. 4,276,280), fluorinated folate chemotherapeutics (U.S. Pat. No. 4,628,090), folate-conjugates with chemotherapeutic agents (Leamon and Reddy, Adv. Drug Deliv. Rev. 2004; 56:1127-41; Leamon et al, Bioconjugate Chem. 2005; 16:803-11), with proteins and protein toxins (Ward et al., J. Drug Target. 2000; 8:119-23; Leamon et al, J. Biol. Chem. 1993; 268:24847-54; Leamon and Low, J. Drug Target. 1994; 2:101-12), with antisense oliconucleotides (Li et al, Pharm. Res. 1998; 15:1540-45; Zhao and Lee, Adv. Drug Deliv. Rev. 2004; 56:1193-204), with liposomes (Lee and Low, Biochim. Biophys. Acta-Biomembr. 1995; 1233:134-44; Gabizon et al, Adv. Drug Deliv. Rev. 2004; 56:1177-92), with hapten molecules (Paulos et al, Adv. Drug Deliv. Rev. 2004; 56:1205-17), with MRI contrast agents (Konda et al, Magn. Reson. Mat. Phys. Biol. Med. 2001; 12:104-13) etc.

Folate radiopharmaceuticals can be in particular very useful for an improved diagnosis and evaluation of the effectiveness of cancer and inflammatory and autoimmune disease therapy. This may include assessment and/or prediction of a treatment response and consequently improvement of radiation dosimetry. Typical visualization techniques suitable for radioimaging are known in the art and include positron emission tomography (PET), planar or single photon emission computerized tomography (SPECT) imaging, gamma cameras, scintillation, and the like.

Both PET and SPECT use radiotracers to image, map and measure activities of target sites of choice. Yet while PET uses positron emitting nuclides which require a nearby cyclotron, SPECT uses single photon emitting nuclides which are available by generator systems, which may make its use more convenient. However SPECT provides less sensitivity than PET and beside a few approaches quantification methods are lacking. In case of PET, the positron annihilation results in two gamma rays of 511 keV which provide the basis for well developed quantification methods. Thus PET is one of the most sophisticated functional imaging technologies to assess regional uptake and affinity of ligands or metabolic substrates in brain and other organs and thus provides measures of imaging based on metabolic activity. This is for example achieved by administering a positron emitting isotope to a subject, and as it undergoes radioactive decay the gamma rays resulting from the positron/electron annihilation are detected by the PET scanner.

Factors that need to be considered in the selection of a suitable isotope useful for PET include sufficient half-life of the positron-emitting isotope to permit preparation of a diagnostic composition optionally in a pharmaceutically acceptable carrier prior to administration to the patent, and sufficient remaining half-life to yield sufficient activity to permit extra-corporeal measurement by a PET scan. Furthermore, a suitable isotope should have a sufficiently short half-life to limit patient exposure to unnecessary radiation. Typically, a suitable radiopharmaceutical for PET may be based on a metal isotope, such as gallium or copper. These two require however a chelator for entrapment of the metal, which may have an effect on steric and chemical properties. Alternatively a radiopharmaceutical may be based on a covalently linked isotope which provides minimal structural alteration. Radionuclides used for covalent attachment and which could be suitable for PET scanning are typically isotopes with short half lives such as $^{11}$C (ca. 20 min), $^{13}$N (ca. 10 min), $^{15}$O (ca. 2 min), $^{18}$F (ca. 110 min).

To date, a number of chelate-based folate radiopharmaceuticals have been synthesized and successfully evaluated as diagnostic agents for imaging folate receptor-positive tumors (e.g. with $^{111}$In, $^{99m}$Tc and $^{67}$Ga (Leamon et al., Bioconjug Chem 2002, 13 (6):1200; Siegel et al., J. Nucl. Med. 2003, 44:700; Müller et al., J. Organomet. Chem. 2004, 689:4712; Müller et al. Bioconjug Chem 2008, 17(3): 797; Müller et al. Nucl Med Biol 2011, 38 (5): 715) for SPECT or with $^{68}$Ga for PET (Mathias et al., Nucl. Med. Biol. 2003, 30(7):725; Fani et al., Eur J Nucl Med Mol Imaging 2011, 38 (1):108).

In addition, there is growing interest in folate radiopharmaceuticals having a covalently linked isotope, in particular a $^{18}$F-labeled folate radiopharmaceutical because of its excellent imaging characteristics, the long half-life of $^{18}$F (approximately 110 minutes) and because $^{18}$F decays by emitting positrons having the lowest positron energy, which allows for the sharpest images with a high-resolution PET. Furthermore, the longer half-life of $^{18}$F (compared to other isotopes such as $^{68}$Ga) also allows for syntheses that are more complex and satellite distribution to PET centers with no radiochemistry facilities.

To date, reports in the literature include $^{18}$F-labeled folic acid derivatives having the $^{18}$F isotope either directly linked to the folate molecule or through a prosthetic group (WO 2006/071754, WO 2008/098112, WO 2008/125613, WO 2008/125615, WO 2008/125617, Bettio et al., J. Nucl. Med., 2006, 47(7), 1153; Ross et al., Bioconjugate Chem., 2008, 19, 2402, Ross et al., J. Nucl. Med., 2010, 51(11), 1756).

Yet, many methodologies still suffer from drawbacks including time-consuming radiosyntheses giving low radiochemical yields, or unfavorable pharmacokinetics for molecular imaging purposes, and the like.

Thus, there is still a need for specific radiopharmaceuticals suitable for metabolic imaging of tumors to improve diagnosis and treatment of cancer and inflammatory and autoimmune diseases.

Applicants have now found efficient and versatile methods for production of new $^{18}$F-labeled folate radiopharmaceuticals wherein the $^{18}$F isotope is introduced via a prosthetic group, more specifically via a prosthetic group having a saccharide group, such as a cyclic mono- or oligosaccharide, which are preferably based on a pyranoside or furanoside. A prominent member of this group is e.g. 2-$^{18}$F Fluoro-2-deoxy-D-glucose ($^{18}$F-FDG), which is one of the most widely used PET tracer in the world for in vivo assessment of regional glucose metabolic rates in humans. Approved diagnostic uses with PET include its use for determination of myocardial viability and detection of cancer, epilepsy, and Alzheimer's disease. However, there are only very few examples using $^{18}$F-FDG as a building block or prosthetic group for the radiosynthesis of $^{18}$F-labeled compounds.

Applicants have found that the new compounds of the invention are able to overcome the drawbacks of known conjugates and meet the current needs by showing several advantages (due to e.g. their chemical and/or physical characteristics, specifically their hydrophilic character, etc.), such as improved labeling efficiency at low ligand concentration, better biodistribution, increased target tissue uptake and better clearance from non-targeted tissues and organs.

Moreover the new compounds of the invention are obtainable in good yields to meet the expectations for a clinical application in humans. In addition, the new radiosynthesis is applicable in an automated synthesis module which allows a fast and convenient labeling procedure which meets the requirements of GMP guidelines. Preliminary in-vitro and in-vivo studies suggested their suitability as powerful diagnostic agents for FR-positive tumours.

SUMMARY OF THE INVENTION

The present invention is in a first aspect directed to new $^{18}$F-folate-conjugates comprising a folate, and a $^{18}$F-substituted saccharide group, which is linked to either the α-carboxylic acid group or the γ-carboxylic acid group or both the α- and the γ-carboxylic acid group of the folate, more specifically towards compounds of formula I,

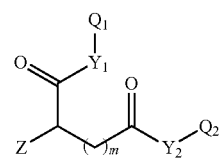

wherein

Z is a pteroate or derivative thereof, $Y_1, Y_2$ are independently of each other O, N or S, m is 1, 2 or 3, and $Q_1, Q_2$ are independently of each other H, a protecting group or a group of formula -L-A-L'-$^{18}$F, wherein L,L' are independently of each other a linking group, such as a covalent bond or a straight-chain or branched C(1-8) alkyl, which is unsubstituted or substituted by at least one CN, Hal, OH, $NH_2$, $CO_2H$, $NO_2$, and wherein one or more of the non-adjacent $CH_2$ groups may independently be replaced by a group selected from —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —SO$_3$R'—, or a five- or six-membered heterocycle, wherein R' represents H or C(1-8)alkyl, and A is a saccharide group, with the proviso that at least one of $Q_1$ and $Q_2$ is a group of formula -L-A-L'-$^{18}$F.

More specifically the present invention is directed towards compounds having formula II

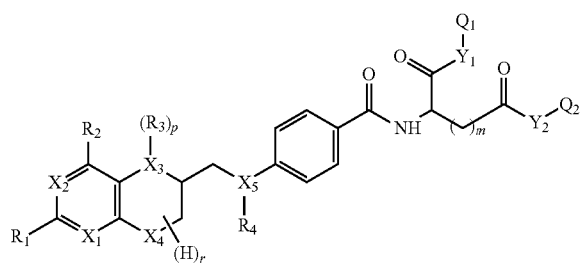

II wherein $X_1$ to $X_5$ are independently of each other C, N or O, preferably N or O, $R_1$, $R_2$ are independently of each other H, halogen, C(1-12)alkyl, C(2-12)alkenyl, C(2-12)alkynyl, —$OR_5$, —$COR_5$, —$COOR_5$, —$NHR_5$, —$CONHR_5$, —$CONHR_5$, wherein $R_5$ represents H, halo, C(1-12)alkyl, C(2-12)alkenyl, C(2-12)alkynyl, —OR', —COR', —COOR', or —NHR', wherein R' is H or C(1-8)alkyl, $R_3$, $R_4$ are independently of each other H, nitroso, C(1-12)alkyl, —OR', —COR' or halosubstituted —COR', wherein R' represents H or C(1-8)alkyl, $Y_1$, $Y_2$ are independently of each other O, N or S, m is 1, 2 or 3, r has a value of 1 to 7, p is 0 or 1, $Q_1$, $Q_2$ are independently of each other H, protecting group or a group of formula -L-A-L'-$^{18}$F, wherein L, L' are independently of each other a linking group, such as a covalent bond or a straight-chain or branched C(1-50) alkyl, which is unsubstituted or substituted by at least one CN, Hal, OH, $NH_2$, $CO_2H$, $NO_2$, and wherein one or more of the non-adjacent $CH_2$ groups may independently be replaced by a group selected from —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —$SO_3$R'—, or a five- or six-membered heterocycle, wherein R' represents H or C(1-8)alkyl, and A is a saccharide group, with the proviso that at least one of $Q_1$ and $Q_2$ is a group of formula -L-A-L'-$^{18}$F.

In specific embodiments the saccharide group is a cyclic monosaccharide or a cyclic oligosaccharide based on a pyranoside, preferably selected from allose, altrose, glucose, mannose, gulose, idose, galactose and talose, or a furanoside, preferably selected from ribose, arabinose, xylose, and lyxose, preferably glucose and galactose.

Thus, in specific embodiments the present invention is directed towards compounds having formula IIIa, IIIb, IIIc, IIIa IIIb -continued

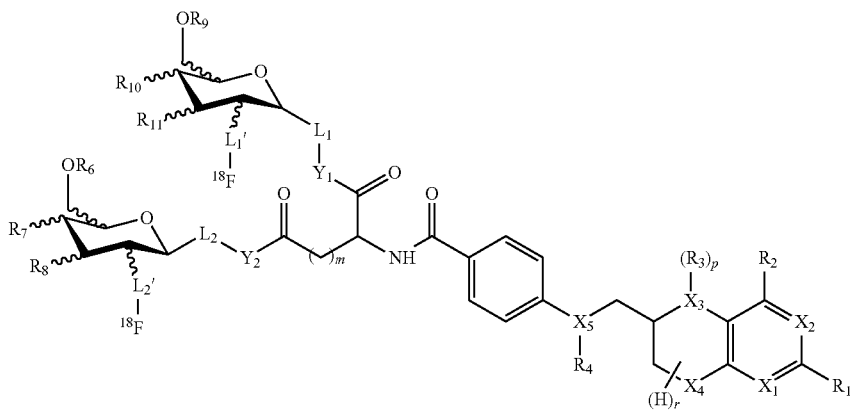

IIIc wherein
$X_1$ to $X_5$ are independently of each other C, N or O, preferably N or O,
$R_1$, $R_2$ are independently of each other H, halogen, C(1-12)alkyl, C(2-12)alkenyl, C(2-12)alkynyl, —OR$_5$, —COR$_5$, —COOR$_5$, —NHR$_5$, —CONHR$_5$, —CONHR$_5$, wherein $R_5$ represents H, halo, C(1-12)alkyl, C(2-12)alkenyl, C(2-12)alkynyl, —OR', —COR', —COOR', or —NHR', wherein R' is H or C(1-8)alkyl,
$R_3$, $R_4$ are independently of each other H, nitroso, C(1-12)alkyl, —OR', —COR' or halosubstituted —COR', wherein R' represents H or C(1-8)alkyl,
$Y_1$,$Y_2$ are independently of each other O, N or S,
m is 1, 2 or 3,
r has a value of 1 to 7,
p is 0 or 1,
$L_1$,$L_1'$,$L_2$,$L_2'$ are independently of each other a linking group, such as a covalent bond or a straight-chain or branched C(1-8)alkyl, which is unsubstituted or substituted by at least one CN, Hal, OH, NH$_2$, CO$_2$H, NO$_2$, and wherein one or more of the non-adjacent CH$_2$ groups may independently be replaced by a group selected from —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —SO$_3$R'—, or a five- or six-membered heterocycle, wherein R' represents H or C(1-8)alkyl,
$B_1$,$B_2$ are independently of each other H, or a protecting group,
$R_6$,$R_9$ is H or C(1-8)alkyl, and
$R_7$,$R_8$,$R_{10}$,$R_{11}$ are independently of each other H, —OH, or —OC(1-8)alkyl.

In specific embodiments the compounds of the invention are in regioisomerically pure form. Thus, in some embodiments the compounds of the invention comprise a $^{18}$F-substituted saccharide group, which is linked to only the α-carboxylic acid group, in other embodiments the compounds of the invention comprise a $^{18}$F-substituted saccharide group, which is linked to only the γ-carboxylic acid group of the folate.

In a further aspect the present invention provides methods for synthesizing a compound of the invention (in regioisomerically pure form or as a mixture of regioisomers).

In yet a further aspect the invention provides pharmaceutical compositions comprising a diagnostic imaging amount optionally together with a therapeutically effective amount of a therapeutic agent of choice and a pharmaceutically acceptable carrier therefor.

In a further aspect the present invention provides uses of the compounds and/or pharmaceutical compositions of the present invention for convenient and effective administration to a subject in need for diagnostic imaging or monitoring of radiotherapy. The subject of the methods of the present invention is preferably a mammal, such as an animal or a human, preferably a human.

In a further aspect the present invention provides a single or multi-vial kit containing all of the components needed to prepare the compounds of this invention, other than the radionuclide ion itself.

Other features and advantages of the invention will be apparent from the following detailed description thereof and from the claims.

DETAILED DESCRIPTION OF THE INVENTION

Figure 1A:
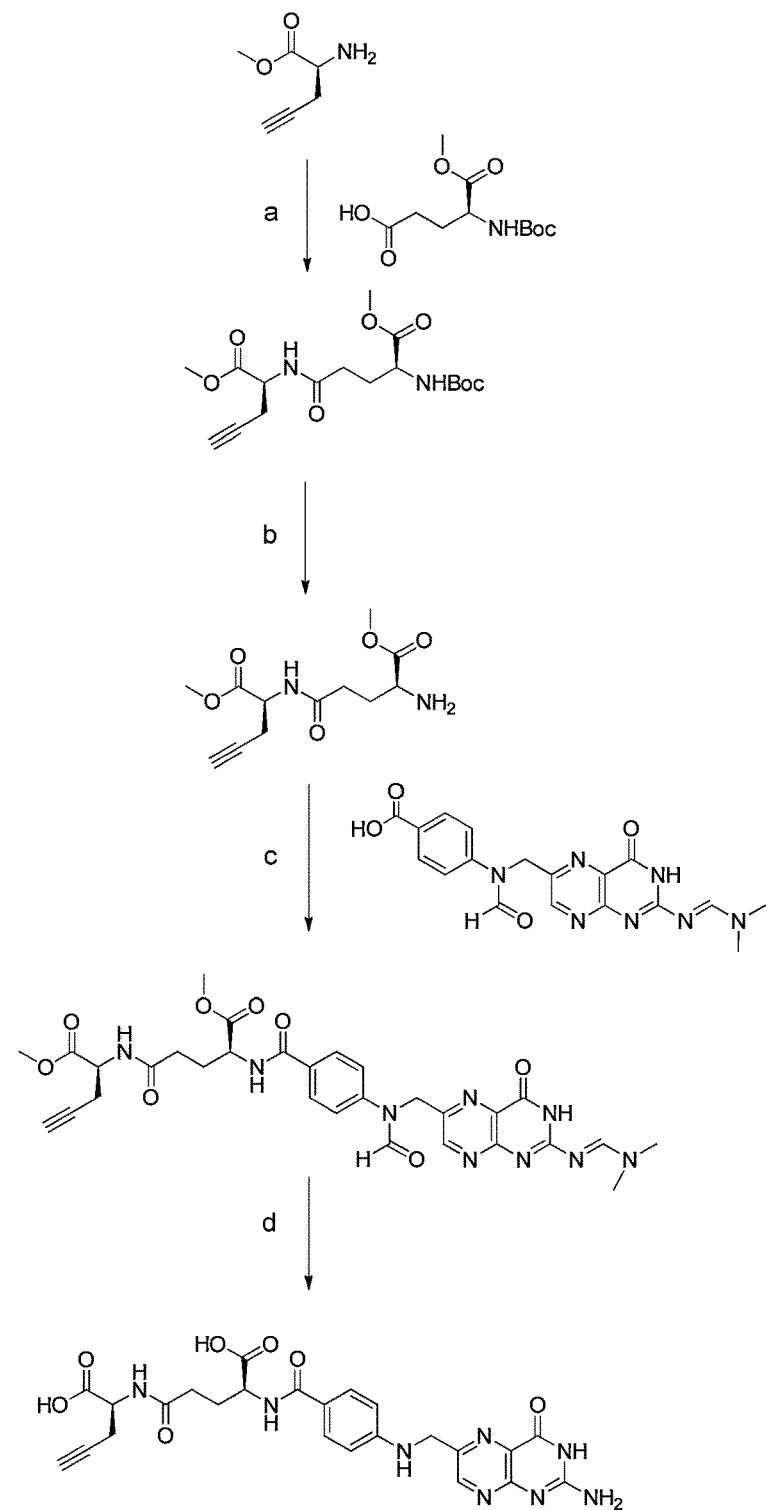
FIG. 1A: Synthesis scheme of γ-folate alkyne precursor.

The present invention is in a first aspect directed to new $^{18}$F-folate-conjugates comprising a pteroate or folate (or derivative thereof), and an $^{18}$F-substituted saccharide group (hereinafter also called compounds of the invention), wherein the $^{18}$F-substituted saccharide group is linked to either the α-carboxylic acid group or the γ-carboxylic acid group or both the α- and the γ-carboxylic acid group of the folate, more specifically towards compounds of formula I,

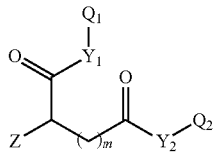

I wherein

Z is a pteroate or derivative thereof,
$Y_1, Y_2$ are independently of each other O, N or S,
m is 1, 2 or 3, and
$Q_1, Q_2$ are independently of each other H, a protecting group, or a group of formula -L-A-L'-$^{18}$F, wherein
L,L' are independently of each other a linking group, such as a covalent bond or a straight-chain or branched C(1-50) alkyl, which is unsubstituted or substituted by at least one CN, Hal, OH, NHR', COOR', $NO_2$, and wherein one or more of the non-adjacent $CH_2$ groups may independently be replaced by a group selected from —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, —$SO_3$R'—, or a five- or six-membered heterocycle, wherein R' represents H or C(1-8)alkyl, and
A is a saccharide group,
with the proviso that at least one of $Q_1$ and $Q_2$ is a group of formula -L-A-L'-$^{18}$F.

More specifically, the compounds of formula I may be represented by compounds having formulae Ia, Ib, Ic,

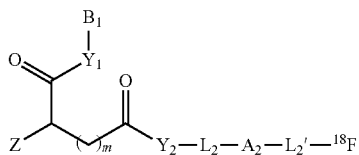

Ia

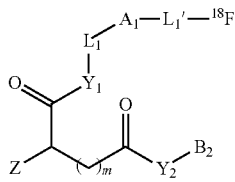

Ib

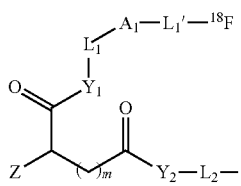

Ic wherein

Z is a pteroate or derivative thereof,
$Y_1, Y_2$ are independently of each other O, N or S,
m is 1, 2 or 3,
$L_1, L_1', L_2, L_2'$ are independently of each other a linking group, such as a covalent bond or a straight-chain or branched C(1-50)alkyl, which is unsubstituted or substituted by at least one CN, Hal, OH, NHR', COOR', $NO_2$, and wherein one or more of the non-adjacent $CH_2$ groups may independently be replaced by a group selected from —O—, —CO—, —CO—O—, —O—CO—, —NR'—, —NR'—CO—, —CO—NR'—, —NR'—CO—O—, —O—CO—NR'—, —NR'—CO—NR'—, —CH═CH—, —C≡C—, —O—CO—O—, —S—R'—, —$SO_3$R'—, or a five- or six-membered heterocycle, wherein R' represents H or C(1-8)alkyl,
$A_1, A_2$ are independently of each other a saccharide group, and
$B_1, B_2$ are independently of each other H, or a protecting group.

Unless specified otherwise all the definitions given hereinafter apply throughout the text (including all structural formulas).

The term "folate" as used herein refers to compounds based on a pteroate group, which is coupled through a peptide bond to a glutamic acid (or derivative thereof). Thus, the term "pteroate" as used herein represents a condensed pyrimidine heterocycle, which is linked to an aminobenzoyl moiety. As used herein a "condensed pyrimidine heterocycle" includes a pyrimidine fused with a further 5- or 6-membered heterocycle, resulting in a pteridine (i.e. a fused 6-6 heterocycle) or a pyrrolopyrimidine bicycle (i.e. a fused 6-heterocycle). Derivatives of a condensed pyrimidine heterocycle include carbocyclic derivatives such as indoles, and isoindoles, quinolines and isoquinolines, and the like. As used herein a "condensed pyrimidine heterocycle, which is linked to an aminobenzoyl moiety" also includes three fused ring systems, i.e. wherein the amino group of the aminobenzoyl moiety forms a further fused ring with the condensed pyrimidine heterocycle, resulting in a fused 6-6-6, 6-6-5, 6-5-6, or 6-5-5 heterocycle. Preferred representatives of folates as used herein are based on a folate skeleton, i.e. pteroyl-glutamic acid resp. N-[4-[[(2-amino-1,4-dihydro-4-oxo-6-pteridinyl)methyl]amino]benzoyl]-L-(or D-)glutamic acid, and derivatives thereof. Thus, as pteroate structures are precursors of folate structures, preferred representatives of pteroates include the analogous derivatives as those typically known for folate structures, which include optionally substituted folic acid, folinic acid, pteropolyglutamic acid, 5,10-methenyl-5,6,7,8-tetrahydrofolate and folate receptor-binding pteridines such as tetrahydropterins, dihydrofolates, tetrahydrofolates, and their deaza and dideaza analogs. Folic acid, 5-methyl-(6S)-tetrahydrofolic acid and 5-formyl-(6S)-tetrahydrofolic acid are the preferred basic structures used for the compounds of this invention. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5-dideaza, 5,10-dideaza, 8,10-dideaza, and 5,8-dideaza analogs. Preferred deaza analogs compounds include N-[4-[2-[(6R)-2-amino-1,4,5,6,7,8-hexahydro-4-oxopyrido[2,3-d]pyrimidin-6-yl]ethyl]benzoyl]-L-glutamic acid (Lometrexol) and N-[4-[1-[(2,4-diamino-6-pteridinyl) methyl]propyl]benzoyl]-L-glutamic acid (Edatrexate).

The term "saccharide group" encompasses both cyclic monosaccharides and cyclic oligosaccharides based on cyclic saccharide unit(s). The term "saccharide unit" as used herein refers to cyclic saccharide units which refer to intracellular cyclic hemiacetal or hemiketal forms of a linear (mono-/oligo-) saccharide. A monosaccharide comprises one saccharide unit, whereas an oligosaccharide refers to a chain of saccharide units and comprises preferably 2 to 20 saccharide units, preferably 2 to 10 saccharide units, more preferably mono-, di-, and trisaccharides. An oligosaccharide may be linear or branched and the saccharide units within the oligosaccharide are linked to each other by alpha- or beta (1-2), (1-4), or (1-6) linkages. Preferably the oligosaccharide of choice is linear, and more preferably the oligosaccharide is linear and the saccharide units within the oligosaccharide are linked by alpha- or beta (1-4) bonds. In the most preferred embodiment, the oligosaccharide is linear and the saccharide units within the oligosaccharide are linked by alpha (1-4) bonds.

Thus in a specific embodiment, A (or $A_1$ and $A_2$) comprises 1 to 10, preferably of 1 to 6, more preferably 1, 2 or 3 saccharide units.

Preferably a saccharide unit is a pyranoside or a furanoside and natural and synthetic derivatives thereof, preferably a pyranoside selected from allose, altrose, glucose, mannose, gulose, idose, galactose, talose and fucose, or a furanoside selected from ribose, arabinose, xylose, and lyxose. The term derivative refers to any chemically or enzymatically modified monosaccharide unit, including those obtained by oxidation, deoxygenation, replacement of one or more hydroxyl groups by preferably a hydrogen atom, a halogen atom, an amino group or thiol group, etc., as well as alkylation, acylation, sulfation or phosphorylation of hydroxy groups or amino groups. Preferred saccharide units of the present invention include for example glucose and galactose.

Thus in one specific embodiment, the saccharide group A (or $A_1$, $A_2$) is a monosaccharide selected from ribose, arabinose, xylose, lyxose, allose, altrose, glucose, mannose, gulose, idose, galactose, talose, fucose, preferably glucose and galactose.

In another specific embodiment, the saccharide group A (or $A_1$, $A_2$) is an oligosaccharide comprising at least two, preferably 2 to 20 saccharide units which are identical or different and each selected from the group consisting of ribose, arabinose, xylose, lyxose, allose, altrose, glucose, mannose, gulose, idose, galactose, talose, fucose, preferably glucose and galactose.

In more specific embodiments an oligosaccharide may be (a) a disaccharide, e.g. lactose, maltose, isomaltose, cellobiose, gentiobiose, melibiose, primeverose, rutinose; (b) a disaccharide homologue, e.g. maltotriose, isomaltotriose, maltotetraose, isomaltotetraose, maltopentaose, maltohexaose, maltoheptaose, lactotriose, lactotetraose; (c) a uronic acid, e.g. glucuronic acid, galacturonic acid; (d) a branched oligosaccharide, e.g. panose, isopanose; (e) an amino monosaccharide, e.g. galactosamine, glucosamine, mannosamine, fucosamine, quinovosamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine, rhodosamine; (f) a modified saccharide, e.g. abequose, amicetose, arcanose, ascarylose, boivinose, chacotriose, chalcose, cladinose, colitose, cymarose, 2-deoxyribose, 2-deoxyglucose, diginose, digitalose, digitoxose, evalose, evernitrose, hamamelose, manninotriose, melibiose, mycarose, mycinose, nigerose, noviose, oleandrose, paratose, rhodinose, rutinose, sarmentose, sedoheptulose, solatriose, sophorose, streptose, turanose, tyvelose.

In a more preferred embodiment, the saccharide group A (or $A_1$, $A_2$) is a monosaccharide or an oligosaccharide, thus comprising one or more of the (same or different) saccharide unit(s) which is (are) selected from the group consisting of glucose, galactose, glucosamine, galactosamine, glucuronic acid, gluconic acid, galacturonic acid, lactose, lactotetraose, maltose, maltotriose, maltotetraose, isomaltose, isomaltotriose, isomaltotetraose, and neuraminic acid.

The saccharide group A, or $A_1$ and $A_2$, are substituted with at least one $^{18}F$ atom, which can be linked either directly through a covalent bond or through a linker L' (or $L_1$' and $L_2$') as defined herein, to at least one saccharide unit. In case of oligosaccharides, the 18F-atom may be linked to any of the saccharide units within the oligosaccharide, preferably to the terminal saccharide unit in A, or $A_1$ and $A_2$. A terminal saccharide unit refers to the saccharide unit that is linked to either none (in case of a monosaccharide) or only one neighbouring saccharide unit (in case of an oligosaccharide). It is understood that all isomers, including enantiomers, diastereoisomers, rotamers, tautomers, regiosiomers and racemates of the compounds of the invention are contemplated as being part of this invention. The invention includes stereoisomers in optically pure form and in admixture, including racemic mixtures. Isomers can be prepared using conventional techniques, either by reacting optically pure or optically enriched starting materials or by separating isomers of a compound of formula I. This applies specifically to group A (or A1, A2) which refers to a saccharide group, or the amino acid groups present in a compound of formula I (and subsequent formulas), which may be present in the natural L- or non-natural D-form, i.e. the glutamic acid portion (or derivatives thereof). The invention also includes regioisomers in pure form, i.e. compounds of the invention with the same empirical formula, but with a different attachment of groups Q1 and Q2, more specifically wherein the $^{18}F$-substituted saccharide group is linked to only the α-carboxylic acid group (i.e. the α-regioisomer), or only the γ-carboxylic acid group of the folate (i.e. the γ-regioisomer). While at times, there is preference to one specific attachment site (α or γ) only, thereby producing two regioisomers in pure form, the present invention also includes mixtures of both regioisomers as well as compounds of the invention wherein both sites are substituted with $^{18}F$-substituted saccharide group.

More specifically, the present invention is directed towards compounds of formula II

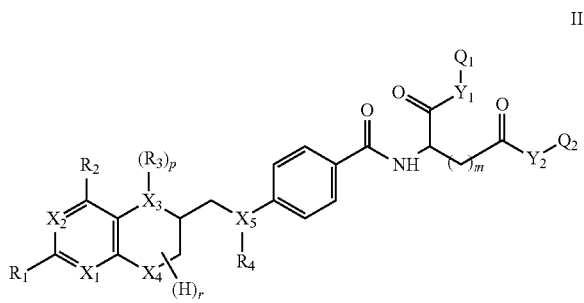

II wherein $X_1$ to $X_5$ are independently of each other C, N or O, preferably N or O, $R_1$, $R_2$ are independently of each other H, halogen, C(1-12)alkyl, C(2-12)alkenyl, C(2-12)alkynyl, —$OR_5$, —$COR_5$, —$COOR_5$, —$NHR_5$, —$CONHR_5$, —$CONHR_5$, wherein $R_5$ represents H, halo, C(1-12)alkyl, C(2-12)alkenyl, C(2-12)alkynyl, —OR', —COR', —COOR', or —NHR', wherein R' is H or C(1-8)alkyl, $R_3$, $R_4$ are independently of each other H, nitroso, C(1-12)alkyl, —OR', —COR' or halosubstituted —COR', wherein R' represents H or C(1-8)alkyl, $Y_1$, $Y_2$ are independently of each other O, N or S, m is 1, 2 or 3, r has a value of 1 to 7, p is 0 or 1, $Q_1$, $Q_2$ are independently of each other H, a protecting group, or a group of formula -L-A-L'-$^{18}$F, wherein L,L' are independently of each other a linking group, such as a covalent bond or a straight-chain or branched C(1-50) alkyl, which is unsubstituted or substituted by at least one CN, Hal, OH, NHR', COOR', NO$_2$, and wherein one or more of the non-adjacent CH$_2$ groups may independently be replaced by a group selected from —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —SO$_3$R'—, or a five- or six-membered heterocycle, wherein R' represents H or C(1-8)alkyl, and A is a saccharide group, with the proviso that at least one of $Q_1$ and $Q_2$ is a group of formula -L-A-L'-$^{18}$F.

As outlined above for compounds of formula I, the compounds of formula II may be represented by compounds having formulae IIa, IIb, IIc —COR$_5$, —COOR$_5$, —NHR$_5$, —CONHR$_5$, —CONHR$_5$, wherein R$_5$ represents H, halo, C(1-12)alkyl, C(2-12)alkenyl, C(2-12)alkynyl, —OR', —COR', —COOR', or —NHR', wherein R' is H or C(1-8)alkyl, R$_3$, R$_4$ are independently of each other H, nitroso, C(1-12)alkyl, —OR', —COR' or halosubstituted —COR', wherein R' represents H or C(1-8)alkyl, $Y_1$,$Y_2$ are independently of each other O, N or S, m is 1, 2 or 3, r has a value of 1 to 7, p is 0 or 1, $L_1$,$L_1$',$L_2$,$L_2$' are independently of each other a linking group, such as a covalent bond or a straight-chain or branched C(1-50)alkyl, which is unsubstituted or substituted by at least one CN, Hal, OH, NHR', COOR', NO$_2$, and wherein one or more of the non-adjacent CH$_2$ groups may independently be replaced by a group selected from —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—,

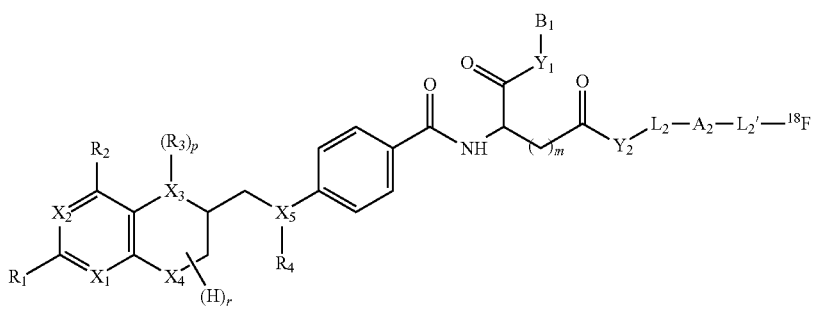

IIa

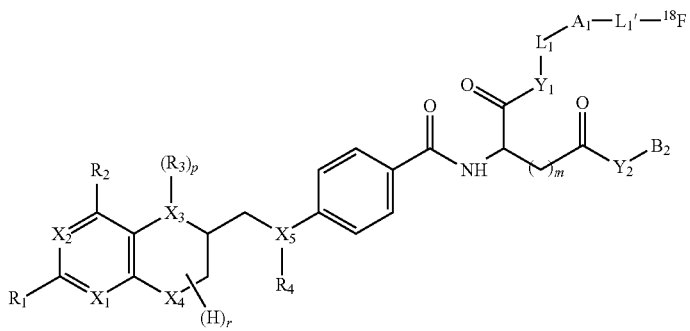

IIb

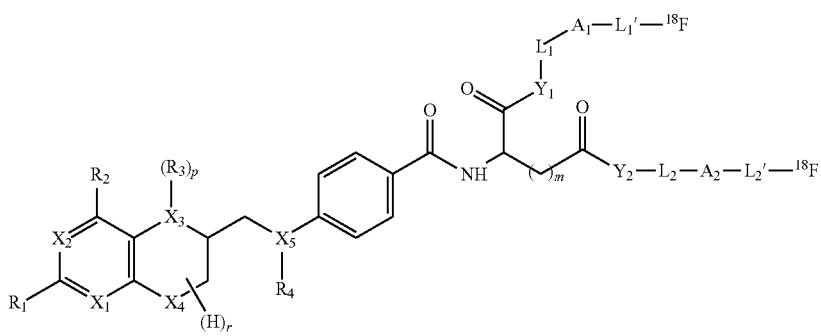

IIc wherein $X_1$ to $X_5$ are independently of each other C, N or O, preferably N or O, $R_1$, $R_2$ are independently of each other H, halogen, C(1-12)alkyl, C(2-12)alkenyl, C(2-12)alkynyl, —OR$_5$, —O—CO—O—, —S—R'—, —SO$_3$R'—, or a five- or six-membered heterocycle, wherein R' represents H or C(1-8)alkyl, $A_1$,$A_2$ are independently of each other a saccharide group, and B$_1$,B$_2$ are independently of each other H, or a protecting group.

It is understood, that the abbreviations "N" and "C" are representative for all possible degrees of saturation, i.e. N includes —NH— and —N= linkages and C includes —CH$_2$— and —CH= linkages.

It is further understood, that (H)$_q$ represents all hydrogen substituents on the indicated ring (i.e. on X$_3$, C6, C7 and X$_4$). For example q=7 for a fully saturated 5,8-dideaza analog (X$_3$=X$_4$=C) and q=1 for a fully unsaturated analog with X$_3$=X$_4$=N.

The term "alkyl", when used singly or in combination, refers to straight chain or branched alkyl groups containing the indicated number of carbon atoms. Thus, the term "C(1-12)alkyl" refers to a hydrocarbon radical whose carbon chain is straight-chain or branched and comprises 1 to 12 carbon atoms. Preferred alkyl groups include C(1-8)alkyl groups (such as for group Sp) which refer to a hydrocarbon radical whose carbon chain is straight-chain or branched and comprises 1 to 8 carbon atoms, for example methyl, ethyl, propyl, isopropyl, butyl, sec-butyl, isobutyl, tertiary butyl, pentyl, isopentyl, neopentyl, hexyl, 2,3-dimethylbutane, neohexyl, heptyl, octyl. More preferred alkyl groups are C(1-6)alkyl groups containing one to six C-atoms, more preferably one to four carbon atoms.

The term "alkenyl", singly or in combination with other groups, refers to straight chain or branched alkyl groups as defined hereinabove having one or more carbon-carbon double bonds. Thus, the term "C(2-12)alkenyl" refers to a hydrocarbon radical whose carbon chain is straight-chain or branched and comprises 1 to 12 carbon atoms and one or more carbon-carbon double bonds. Preferred alkenyl groups include C(2-8)alkenyl groups, such as methylene, ethylene, propylene, isopropylene, butylene, t-butylene, sec-butylene, isobutylene, amylene, isoamylene, pentylene, isopentylene, hexylene and the like. The preferred alkenyl groups contain two to six, more preferably two to four carbon atoms.

The term "alkynyl" as used herein refers to a linear or branched alkyl groups as defined hereinabove having one or more carbon-carbon triple bonds. The preferred alkynyl groups contain two to six, more preferably two to four carbon atoms.

The term "halogen" as used herein refers to any Group 7 element and includes fluoro, chloro, bromo, iodo.

The term "halosubstituted" as used herein refers to alkyl groups which have halogen moieties in the place of at least one hydrogen.

In preferred embodiments, R$_1$ and R$_2$ may be independently of each other H, C(1-12)alkyl, —OR$_5$, —NHR$_5$, more preferably —OR$_5$, —NHR$_5$, wherein R$_5$ is H, halo, C(1-12)alkyl, C(2-12)alkenyl, C(2-12)alkynyl, —OR', —COR', —COOR', or —NHR', wherein R' is H or C(1-8) alkyl; and/or R$_3$ is H, C(1-12)alkyl, or —CO—C(1-8)alkyl; and/or R$_4$ is H, nitroso, —O—C(1-8)alkyl, or —CO—C(1-8)alkyl.

Coupling chemistries known and described in the art may be used for conjugation of the 18F isotope to the saccharide group to the folate compound via linking groups L (or L$_1$, L$_2$) and L' (or L$_1$', L$_2$') of the compounds of the invention. Such procedures are within the average skill of a skilled person and require only routine experimentation and optimization of standard synthesis strategies available in the prior art.

Typical coupling strategies include reactions between amine, alcohol, or thiol functional groups with aldehyde, carboxylic acid or activated carboxylic acid functional groups or cycloaddition reactions such as the click reaction.

A skilled person will know which desired functional group have to be present as terminal groups of the linkers L (or L$_1$, L$_2$) and L' (or L$_1$', L$_2$') of choice. Preferred coupling strategies include e.g. standard peptide coupling chemistry, whereby an amine is reacted with a carboxylic acid using for example EDC, DCC, pyBOP or other carboxylate activating agents to form an amide linkage, or cycloaddition reactions, e.g. click-chemistry based couplings, whereby an azide group is reacted with an alkyne to form an azaheterocycle.

Groups L$_1$, L$_1$', L$_2$ and L$_2$' are independently of each other a covalent bond or a straight-chain or branched C(1-50) alkyl, which is unsubstituted or substituted by at least one group selected from Hal, OH, NHR', CO$_2$R', and wherein one or more of the non-adjacent CH$_2$ groups may independently be replaced by a group selected from —O—, —CO—O—, —O—CO—, —NR'—, —NR'—CO—, —CO—NR', or a five- or six-membered heterocycle, wherein R' represents H or C(1-8)alkyl. The expression "a straight-chain or branched C(1-50)alkyl, which is unsubstituted or substituted by at least one group selected from Hal, OH, NHR', CO$_2$R', and wherein one or more of the non-adjacent CH$_2$ groups may independently be replaced by a group selected from —O—, —CO—O—, —O—CO—, —NR'—, —NR'—CO—, —CO—NR'" also includes linking groups such as hydrophilic oligo/polymeric groups, such as oligo/polyethers, oligo/polypeptides, oligo/polyamides, oligo/polyamines, oligo/polyesters, oligo/polysaccharides, polyols, multiple charged species or any other combinations thereof.

In one embodiment, such a hydrophilic oligo/polymeric group includes an oligo/polyether such as oligo/polyalkyleneoxide, more specifically polyethyleneglycol (PEG) and related homopolymers, such as polymethylethyleneglycol, polyhydroxypropyleneglycol, polypropyleneglycol, polymethylpropyleneglycol, and polyhydroxypropyleneoxide, or heteropolymers of small alkoxy monomers, such as a polyethetylene/polypropyleneglycol, typically having from 2 to 25, preferably from 2 to 10 oxyalkylene groups.

In another embodiment such a hydrophilic oligo/polymeric group includes an oligo/polypeptide such as a hydrophilic peptide sequence or a polyaminoacids and derivatives thereof, e.g., polyglutamic acids, polylysines, polyaspartic acids, polyaspartamides, wherein each peptide sequence or polyaminoacid typically has from 2 to 12, preferably 2 to 6 amino acid residues.

Preferably, L$_1$ and L$_2$ are straight-chain or branched C(1-24), more preferably C(1-12), most preferably C(1-6)alkyl, which is unsubstituted or substituted by at least one group selected from OH, NHR', CO$_2$R', and wherein one or more of the non-adjacent CH$_2$ groups may independently be replaced by a five- or six-membered heterocycle, preferably a five-membered azaheterocycle such as a triazole or a tetrazole, wherein R' represents H or C(1-8)alkyl, or a hydrophilic oligo/polymeric group as defined above.

Groups L$_1$' and L$_2$' are preferably a covalent bond or a straight-chain or branched C(1-24)alkyl, more preferably C(1-12)alkyl, most preferably C(1-6)alkyl, which is unsubstituted or substituted by at least one group selected from Hal, OH, NHR', CO$_2$R', and wherein one or more of the non-adjacent CH$_2$ groups may independently be replaced by a group selected from —O—, —CO—O—, —O—CO—, —NR'—, —NR'—CO—, —CO—NR', wherein R' represents H or C(1-8)alkyl.

More preferably, L$_1$' and L$_2$' are a covalent bond or a straight-chain or branched C(1-12)alkyl, more preferably C(1-6)alkyl, wherein one or more of the non-adjacent CH$_2$ groups may independently be replaced by a group selected from —O—, —CO—O—, —O—CO—, —NR'—, —NR'—CO—, —CO—NR', wherein R' represents H or C(1-8)alkyl.

Group m is 1, 2, or 3, preferably 2.

In specific embodiments, $Y_1$ and/or $Y_2$ are preferably N and thus $B_2$ is a carboxamide protecting group.

The term "protecting group" (or terminal groups) as used herein refers to a suitable protecting group for $Y_1$ and/or $Y_2$. These protecting groups depend on the nature of the functional group (typically an amino or carboxamide, carboxyl or thiocarbonyl function) and thus are variable. Suitable protecting groups for amino functions include e.g. the t-butoxycarbonyl, the benzyloxycarbonyl, allyloxycarbonyl, methoxy- or ethoxycarbonyl, 2,2,2-trichloroethoxycarbonyl, acetyl or trifluoroacetyl, benzyl or 2,4,6-trimethoxybenzyl, the phthaloyl group, and the trityl or tosyl protecting group. Suitable protecting groups for an amide function include e.g. p-methoxyphenyl, 3,4-dimethoxybenzyl, benzyl, 0-nitrobenzyl, di-(p-methoxyphenyl)methyl, triphenylmethyl, (p-methoxyphenyl)diphenylmethyl, diphenyl-4-pyridylmethyl, m-2-(picolyl)-N'-oxide, 5-dibenzosuberyl, trimethylsilyl, t-butyl dimethylsilyl, and the like. Suitable protecting groups for the carboxyl function include e.g. silyl groups and alkyl, aryl or arylalkyl esters, more specifically alkyl esters such as methyl and t-butyl; alkoxyalkyl such as methoxymethyl; alkyl thioalkyl esters such as methyl, thiomethyl; haloalkyl esters such as 2,2,2-trichloroethyl and aralkyl ester, such as benzyl, p-methoxybenzyl, p-nitrobenzyl, diphenylmethyl. Suitable protecting groups for the hydroxy function include e.g. alkyl esters, t-butyl, benzyl or trityl groups, including methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether)), substituted ethyl ethers, substituted benzyl ethers, silyl ethers (e.g., TMS (trimethylsilyl ether), TES (triethylsilyl ether), TIPS (triisopropylsilyl ether), TBDMS (tert-butyldimethylsilyl ether), tribenzyl silyl ether, TBDPS (tert-butyldiphenylsilyl ether)). The present invention is not intended to be limited to these protecting groups; rather, a variety of additional equivalent protecting groups can be readily identified and utilized in the present invention. The above and further protecting groups as well as techniques to introduce and remove them are described in "Protective Groups in Organic Synthesis" Third Ed. Greene, T. W. and Wuts, P. G., Eds., John Wiley & Sons, New York: 1999, the entire contents of which are hereby incorporated by reference.

In more specific embodiments the present invention is directed towards compounds of formulae IIIa, IIIb, IIIc

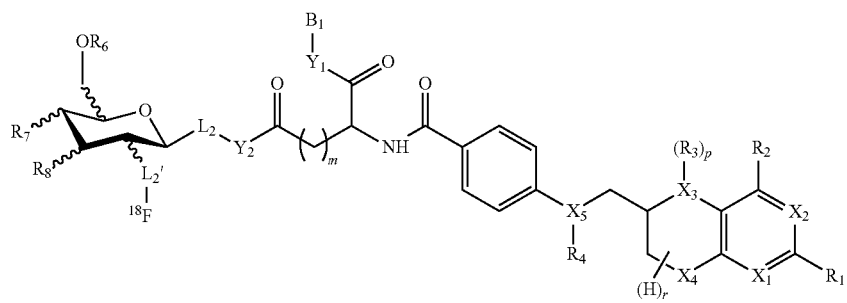

IIIa

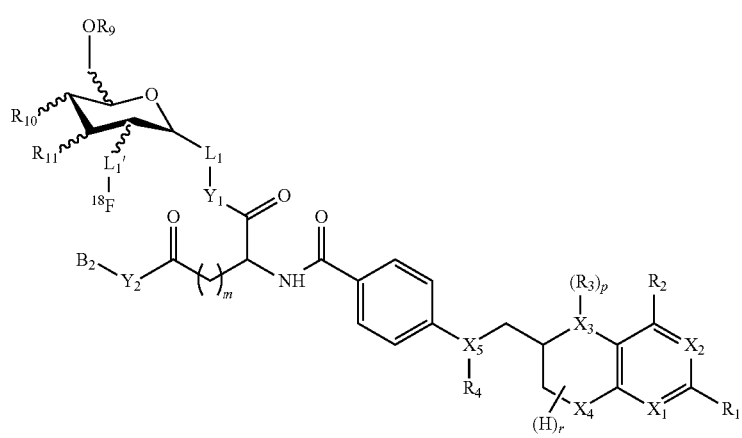

IIIb

-continued

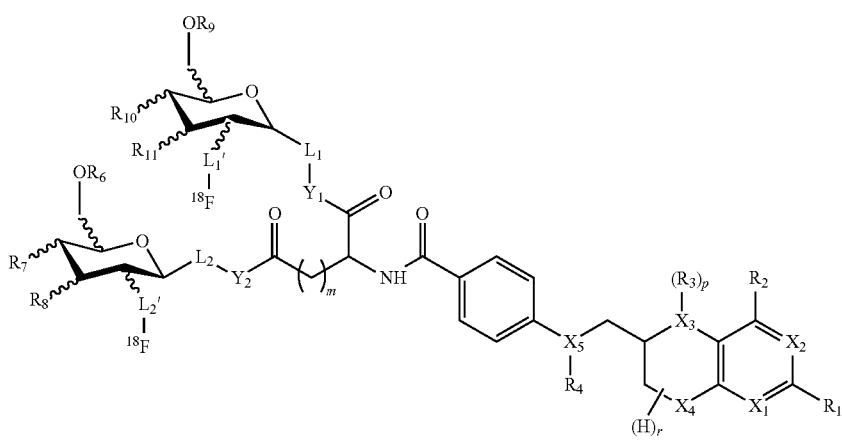

IIIc wherein $X_1$ to $X_5$ are independently of each other C, N or O, preferably N or O, $R_1$, $R_2$ are independently of each other H, halogen, C(1-12)alkyl, C(2-12)alkenyl, C(2-12)alkynyl, —$OR_5$, —$COR_5$, —$COOR_5$, —$NHR_5$, —$CONHR_5$, —$CONHR_5$, wherein $R_5$ represents H, halo, C(1-12)alkyl, C(2-12)alkenyl, C(2-12)alkynyl, —OR', —COR', —COOR', or —NHR', wherein R' is H or C(1-8)alkyl, $R_3$, $R_4$ are independently of each other H, nitroso, C(1-12)alkyl, —OR', —COR' or halosubstituted —COR', wherein R' represents H or C(1-8)alkyl, $Y_1, Y_2$ are independently of each other O, N or S, m is 1, 2 or 3, r has a value of 1 to 7, p is 0 or 1, $L_1, L_1', L_2, L_2'$ are independently of each other a linking group, such as a covalent bond or a straight-chain or branched C(1-8)alkyl, which is unsubstituted or substituted by at least one CN, Hal, OH, NHR', COOR', $NO_2$, and wherein one or more of the non-adjacent $CH_2$ groups may independently be replaced by a group selected from —O—, —CO—, —CO—O—, —O—CO—, —NR'—, —NR'—CO—, —CO—NR'—, —NR'—CO—O—, —O—CO—NR'—, —NR'—CO—NR'—, —CH=CH—, —C≡C—, —O—CO—O—, —S—R'—, —$SO_3$R'—, or a five- or six-membered heterocycle, wherein R' represents H or C(1-8)alkyl, $B_1, B_2$ are independently of each other H, or a protecting group, $R_6, R_9$ is H or C(1-8)alkyl, and $R_7, R_8, R_{10}, R_{11}$ are independently of each other H, —OH, or —OC(1-8)alkyl.

The term "heterocycle" (or "heterocyclic ring"), as used herein, means any 4- to 7-membered heterocyclic ring which is either saturated, unsaturated, or aromatic, and which contains from 1 to 3 heteroatoms independently selected from nitrogen, oxygen and sulfur, and wherein the nitrogen and sulfur heteroatoms may be optionally oxidized, and the nitrogen heteroatom may be optionally quaternized. Heterocycles may include, but are not limited to, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like. Preferred heterocylces for use in the present invention are azaheterocycles containing containing from 1 to 3 nitrogen atoms, preferably five-membered azaheterocycles. The term "azaheterocycle" as used in connection with $L_1$, $L_1'$ and $L_2$, $L_2'$ and preferably in connection with $L_1$ and $L_2$ refers to a heterocyclic group which includes at least one nitrogen atom in a ring and may be unsubstituted or substituted. The azaheterocyclic group may also be substituted as recognized in the art, e.g. by a C(1-6)alkyl. For use in the present compounds, a five-membered azaheterocyclic group is preferred, such as a triazolyl or tetrazolyl group, more preferably a group of the following structures

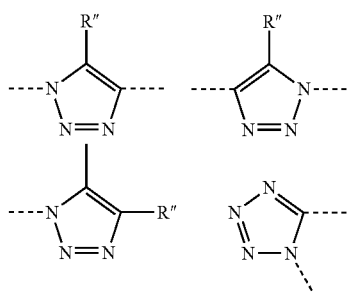

wherein the dotted lines represent linking sites to the adjacent groups and R" is H or a straight-chain or branched C(1-8)alkyl, which is unsubstituted or substituted by at least one CN, Hal, or $NO_2$.

Thus in preferred embodiments, $L_1$, $L_1'$, $L_2$ and $L_2'$ and preferably $L_1$ and $L_2$ are independently of each other a group of formulae (a), (b), (c) or (d)

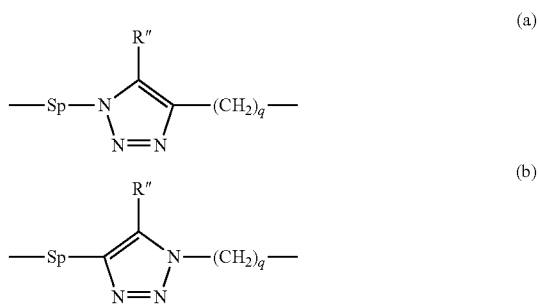

-continued

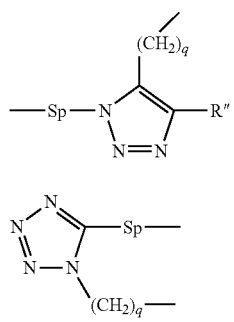

(c)

(d)

wherein

R" is H or a straight-chain or branched C(1-8)alkyl, which is unsubstituted or substituted by at least one CN, Hal, or NO$_2$, Sp is a spacer (linked to Y$_1$ and/or Y$_2$), such as a straight-chain or branched C(1-8)alkyl, which is unsubstituted or wherein at least one of the —CH$_2$— groups is substituted with —OH, —NHR', or —COOR', wherein R' represents H or C(1-8)alkyl and, q is 0, 1, 2, 3 or 4.

In preferred embodiments, Sp is a straight-chain or branched C(1-6)alkyl, which is unsubstituted or wherein at least one of the —CH$_2$— groups is substituted with —OH, NHR', or COOR', wherein R' is as defined above.

Thus in some embodiments the present invention provides compounds of formula I having formulae IVa, IVb, IVc, IVd

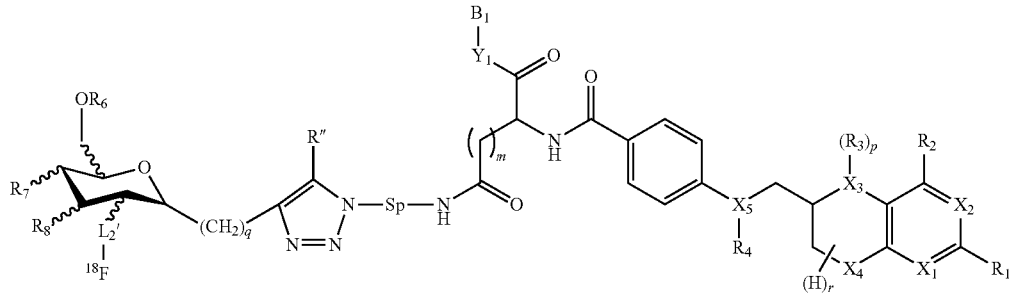

IVa

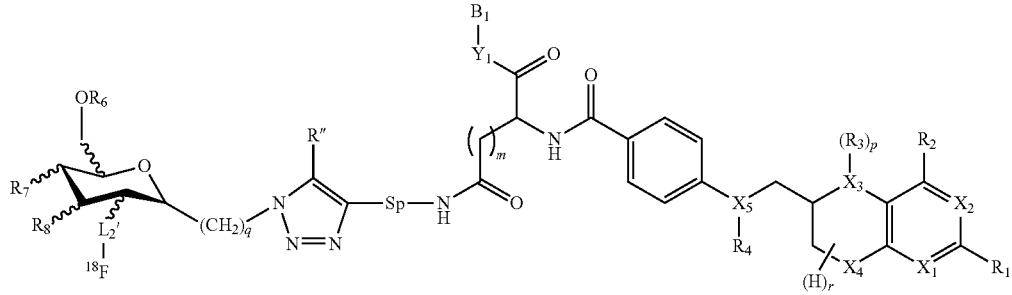

IVb

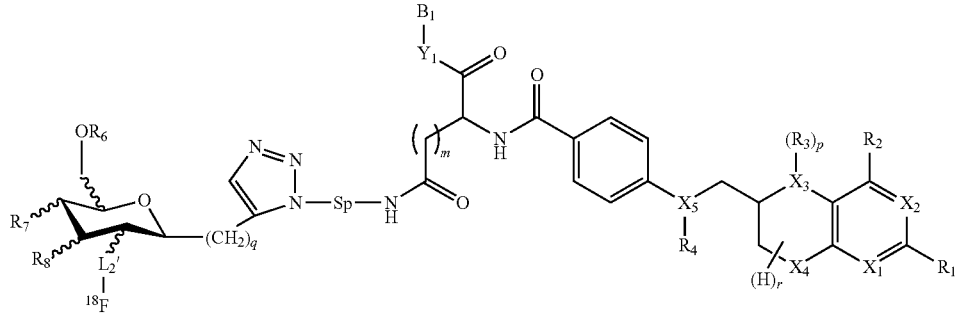

IVc

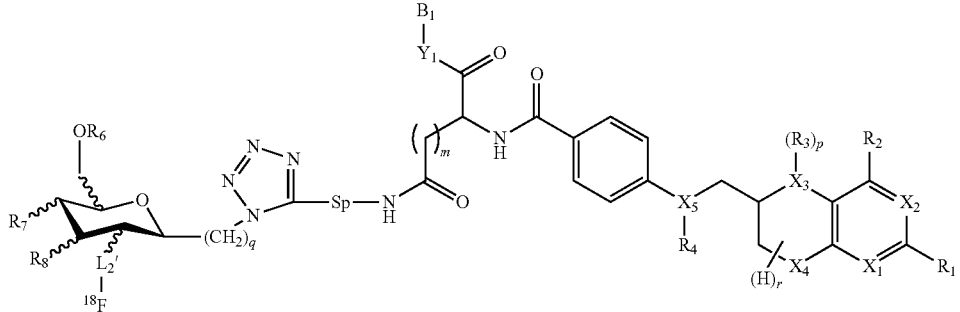

IVd wherein $X_1$ to $X_5$ are independently of each other C, N or O, preferably N or O, $R_1$, $R_2$ are independently of each other H, halogen, C(1-12)alkyl, C(2-12)alkenyl, C(2-12)alkynyl, —$OR_5$, —$COR_5$, —$COOR_5$, —$NHR_5$, —$CONHR_5$, wherein $R_5$ represents H, halo, C(1-12)alkyl, C(2-12)alkenyl, C(2-12)alkynyl, —OR', —COR', —COOR', or —NHR', wherein R' is H or C(1-8)alkyl, $R_3$, $R_4$ are independently of each other H, nitroso, C(1-12)alkyl, —OR', —COR' or halosubstituted —COR', wherein R' represents H or C(1-8)alkyl, m is 1, 2 or 3, r has a value of 1 to 7, p is 0 or 1, $Y_1$ is O, N or S, $B_1$ is H, or a protecting group, R" is H or a straight-chain or branched C(1-8)alkyl, which is unsubstituted or substituted by at least one CN, Hal, or $NO_2$, Sp is a spacer such as a straight-chain or branched C(1-8)alkyl, which is unsubstituted or wherein at least one of the —$CH_2$— groups is substituted with —OH, —NHR', or —COOR', wherein R' represents H or C(1-8)alkyl, $L_2'$ is a covalent bond or a straight-chain or branched C(1-6)alkyl, wherein one or more of the non-adjacent $CH_2$ groups may independently be replaced by a group selected from —O—, —O—, —O—CO—, —NR'—, —NR'—CO—, —CO—NR', wherein R' represents H or C(1-8)alkyl, q is 0, 1, 2, 3 or 4, $R_6$ is H or C(1-8)alkyl, and $R_7$, $R_8$ are independently of each other H, —OH, or —OC(1-8)alkyl.

In other embodiments the present invention provides compounds of formula I having formulae Va, Vb, Vc, Vd

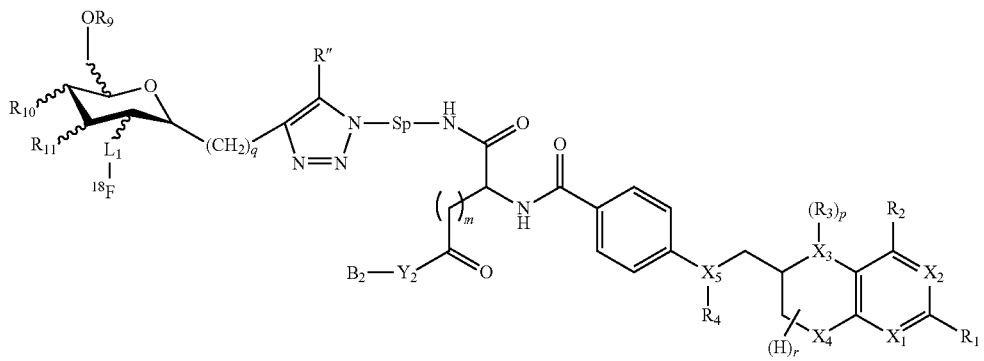

Va

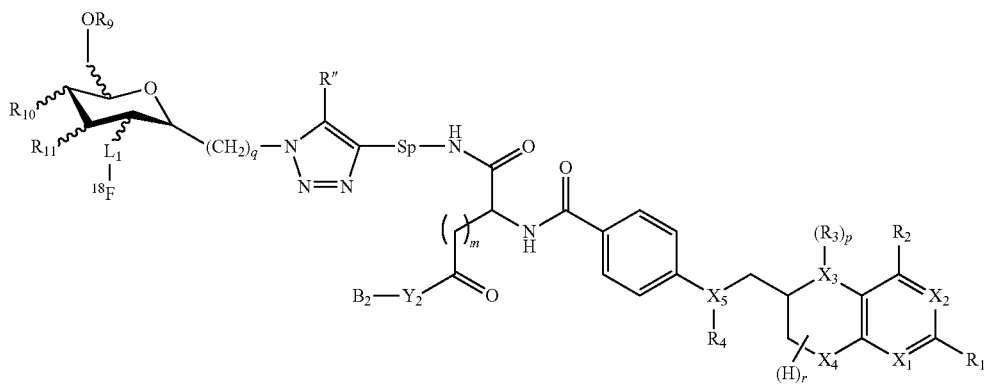

Vb

Vc

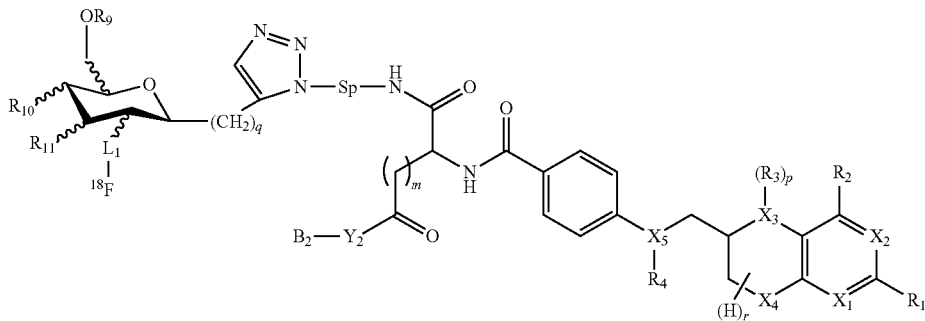

Vd

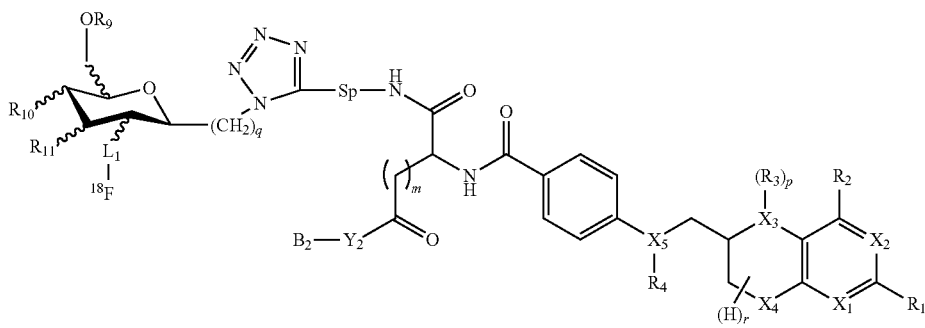

wherein $X_1$ to $X_5$ are independently of each other C, N or O, preferably N or O, $R_1$, $R_2$ are independently of each other H, halogen, C(1-12)alkyl, C(2-12)alkenyl, C(2-12)alkynyl, —$OR_5$, —$COR_5$, —$COOR_5$, —$NHR_5$, —$CONHR_5$, wherein $R_5$ represents H, halo, C(1-12)alkyl, C(2-12)alkenyl, C(2-12)alkynyl, —OR', —COR', —COOR', or —NHR', wherein R' is H or C(1-8)alkyl, $R_3$, $R_4$ are independently of each other H, nitroso, C(1-12)alkyl, —OR', —COR' or halosubstituted —COR', wherein R' represents H or C(1-8)alkyl, m is 1, 2 or 3, r has a value of 1 to 7, p is 0 or 1, $Y_2$ is O, N or S, $B_2$ is H, or a protecting group, R" is H or a straight-chain or branched C(1-8)alkyl, which is unsubstituted or substituted by at least one CN, Hal, or $NO_2$, Sp is a spacer such as a straight-chain or branched C(1-8)alkyl, which is unsubstituted or wherein at least one of the —$CH_2$— groups is substituted with —OH, —NHR', or —COOR', wherein R' represents H or C(1-8)alkyl, $L_1'$ is a covalent bond or a straight-chain or branched C(1-6)alkyl, wherein one or more of the non-adjacent $CH_2$ groups may independently be replaced by a group selected from —O—, —CO—O—, —O—CO—, —NR'—, —NR'—CO—, —CO—NR'—, wherein R' represents H or C(1-8)alkyl, q is 0, 1, 2, 3 or 4, $R_9$ is H or C(1-8)alkyl, and $R_{10}$, $R_{11}$ are independently of each other H, —OH, or —OC(1-8)alkyl.

In yet other embodiments the present invention provides compounds of formula I having formulae VIa, VIb, VIc, VId VIa

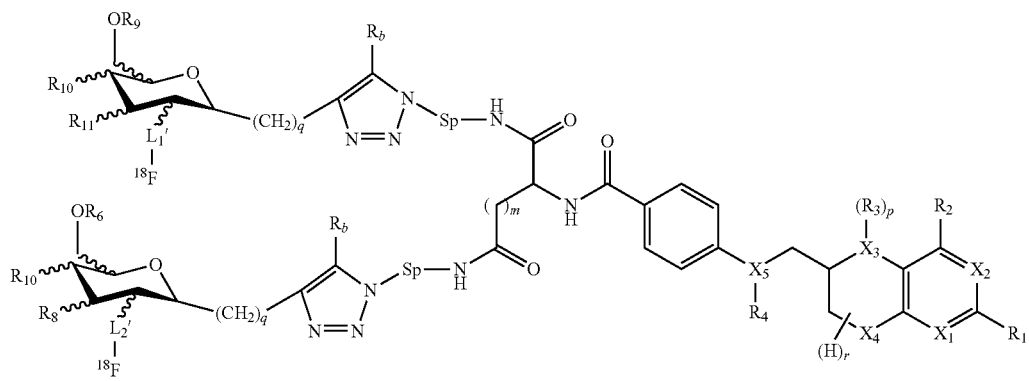

-continued

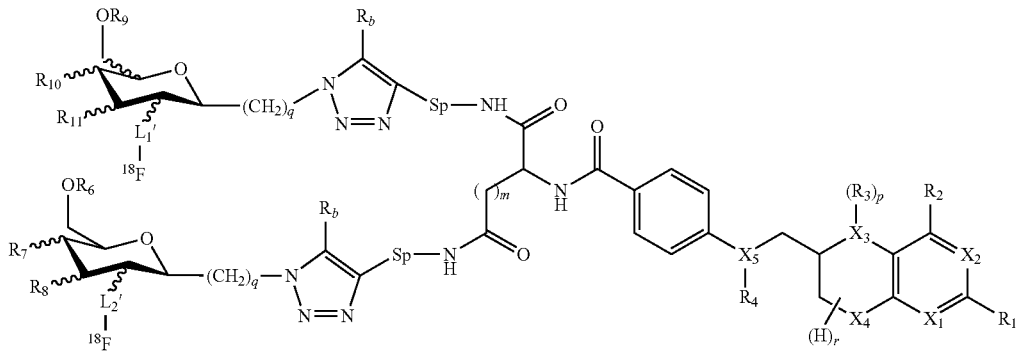

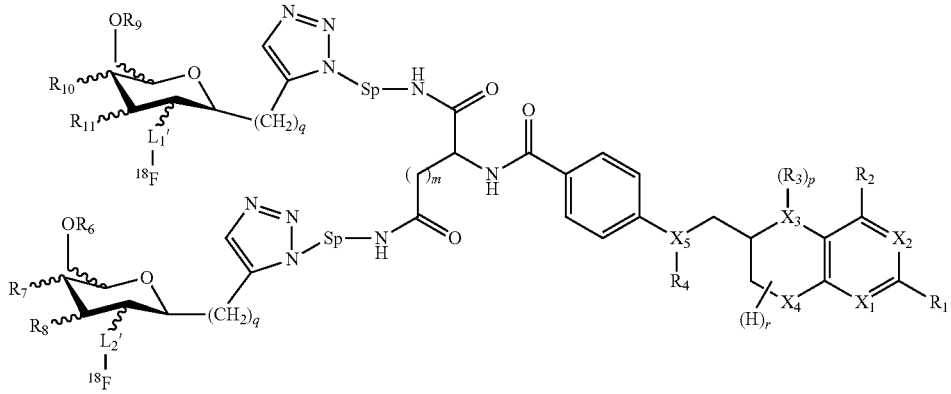

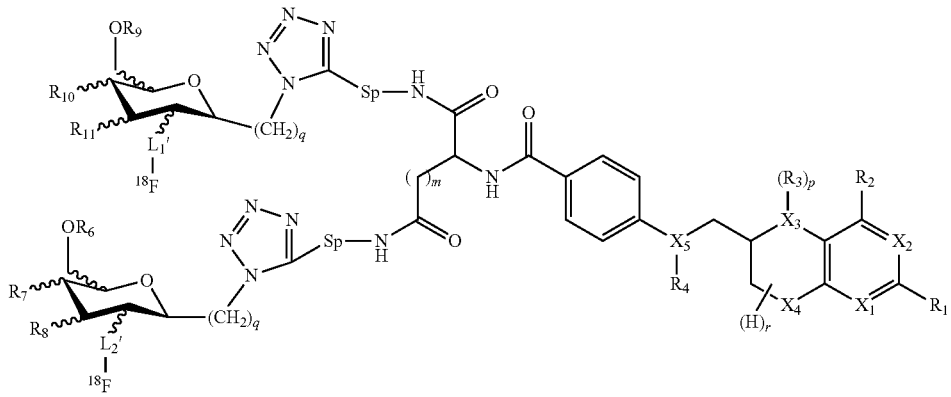

wherein $X_1$ to $X_5$ are independently of each other C, N or O, preferably N or O, $R_1$, $R_2$ are independently of each other H, halogen, C(1-12)alkyl, C(2-12)alkenyl, C(2-12)alkynyl, —$OR_5$, —$COR_5$, —$COOR_5$, —$NHR_5$, —$CONHR_5$, wherein $R_5$ represents H, halo, C(1-12)alkyl, C(2-12)alkenyl, C(2-12)alkynyl, —OR', —COR', —COOR', or —NHR', wherein R' is H or C(1-8)alkyl, $R_3$, $R_4$ are independently of each other H, nitroso, C(1-12)alkyl, —OR', —COR' or halosubstituted —COR', wherein R' represents H or C(1-8)alkyl, m is 1, 2 or 3, r has a value of 1 to 7, p is 0 or 1, R" is H or a straight-chain or branched C(1-8)alkyl, which is unsubstituted or substituted by at least one CN, Hal, or $NO_2$, Sp is a spacer such as a straight-chain or branched C(1-8)alkyl, which is unsubstituted or wherein at least one of the —$CH_2$— groups is substituted with —OH, —NHR', or —COOR', wherein R' represents H or C(1-8)alkyl, $L_1'$, $L_2'$ are independently of each other a covalent bond or a straight-chain or branched C(1-6)alkyl, wherein one or more of the non-adjacent $CH_2$ groups may independently be replaced by a group selected from —O—, —CO—O—, —O—CO—, —NR'—, —NR'—CO—, —CO—NR', wherein R' represents H or C(1-8)alkyl, q is 0, 1, 2, 3 or 4, $R_6$, $R_9$ is H or C(1-8)alkyl, and $R_7$, $R_8$, $R_{10}$, $R_{11}$ are independently of each other H, —OH, or —OC(1-8)alkyl.

One specific embodiment of the compounds of the invention includes for example compounds wherein (a) $X_1$ to $X_5$ are N, $R_1$ is $NY_3Y_4$, $R_2$ is O, $R_4$ is $Y_5$, p is 0 or 1 and q is 1 or 3, or (b) $X_1$ to $X_5$ are N, $R_1$ is $NY_3Y_4$, $R_2$ is $NH_2$, $R_4$ is $Y_5$, p is 0 and q is 1.

Thus in specific embodiments, compounds of the present invention include compounds of formulae VIIa, VIIb, VIIc, VIId

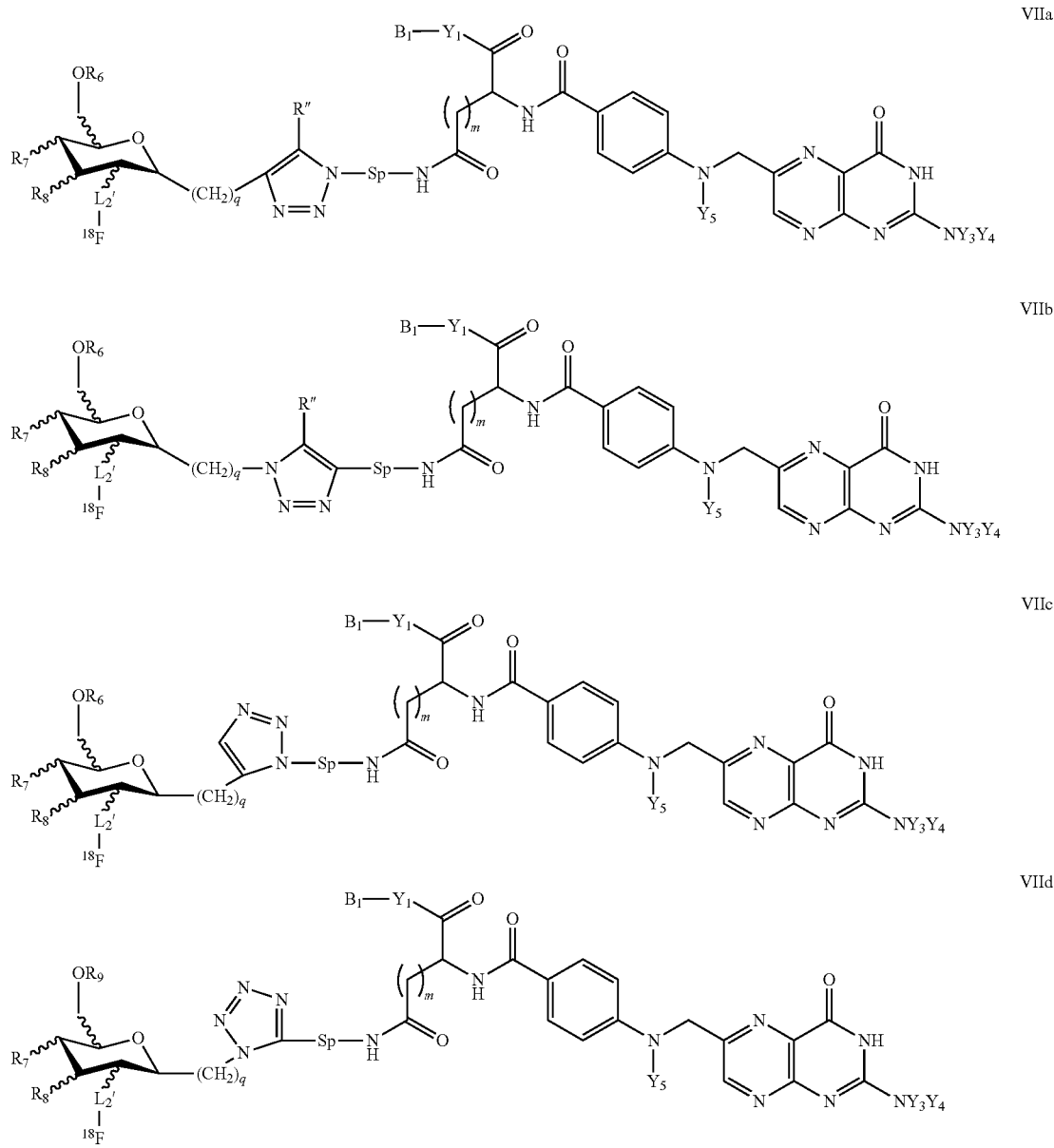

wherein $Y_3$, $Y_4$ are independently of each other selected from H, halo, C(1-12)alkyl, C(2-12)alkenyl, C(2-12)alkynyl, —OR', —COR', —COOR', and —NHR', wherein R' is H or C(1-8)alkyl, $Y_5$ is selected from H, nitroso, C(1-12)alkyl, —OR', —COR', and halosubstituted —COR', wherein R' is H or C(1-12)alkyl, m is 1, 2 or 3, $Y_1$ is O, N or S, $B_1$ is H, or a protecting group, Sp is a spacer such as a straight-chain or branched C(1-8)alkyl, which is unsubstituted or wherein at least one of the —CH$_2$— groups is substituted with —OH, —NHR', or —COOR', wherein R' represents H or C(1-8)alkyl and, $L_2'$ is a covalent bond or a straight-chain or branched C(1-6)alkyl, wherein one or more of the non-adjacent CH$_2$ groups may independently be replaced by a group selected from —O—, —CO—O—, —O—CO—, —NR'—, —NR'—CO—, —CO—NR', wherein R' represents H or C(1-8)alkyl, q is 0, 1, 2, 3 or 4, $R_6$ is H or C(1-8)alkyl, and $R_7$, $R_8$ are independently of each other H, —OH, or —OC(1-8)alkyl.

In other specific embodiments, compounds of the present invention include compounds of formulae VIIIa, VIIIb, VIIIc, VIIId

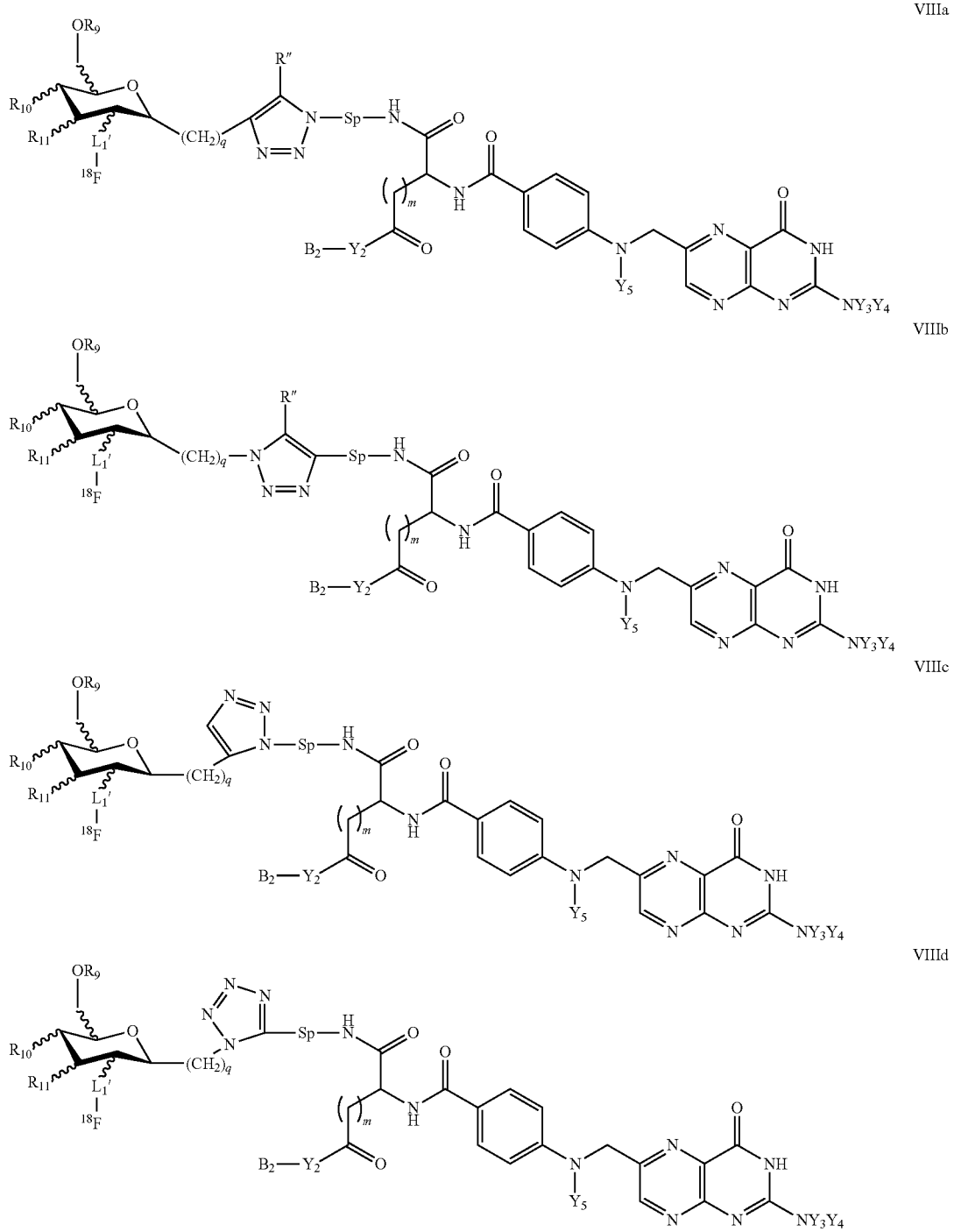

wherein $Y_3$, $Y_4$ are independently of each other selected from H, halo, C(1-12)alkyl, C(2-12)alkenyl, C(2-12)alkynyl, —OR', —COR', —COOR', and —NHR', wherein R' is H or C(1-8)alkyl, $Y_5$ is selected from H, nitroso, C(1-12)alkyl, —OR', —COR', and halosubstituted —COR', wherein R' is H or C(1-12)alkyl, m is 1, 2 or 3, $Y_2$ is O, N or S, $B_2$ is H, or a protecting group, Sp is a spacer such as a straight-chain or branched C(1-8)alkyl, which is unsubstituted or wherein at least one of the —CH$_2$— groups is substituted with —OH, —NHR', or —COOR', wherein R' represents H or C(1-8)alkyl and, $L_2'$ is a covalent bond or a straight-chain or branched C(1-6)alkyl, wherein one or more of the non-adjacent CH$_2$ groups may independently be replaced by a group selected from —O—, —CO—O—, —O—CO—, —NR'—, —NR'—CO—, —CO—NR'—, wherein R' represents H or C(1-8)alkyl, q is 0, 1, 2, 3 or, 4,
R$_9$ is H or C(1-8)alkyl, and
R$_{10}$, R$_{11}$ are independently of each other H, —OH, or —OC(1-8)alkyl
In other specific embodiments, compounds of the present invention include compounds of formulae IXa, IXb, IXc, IXd
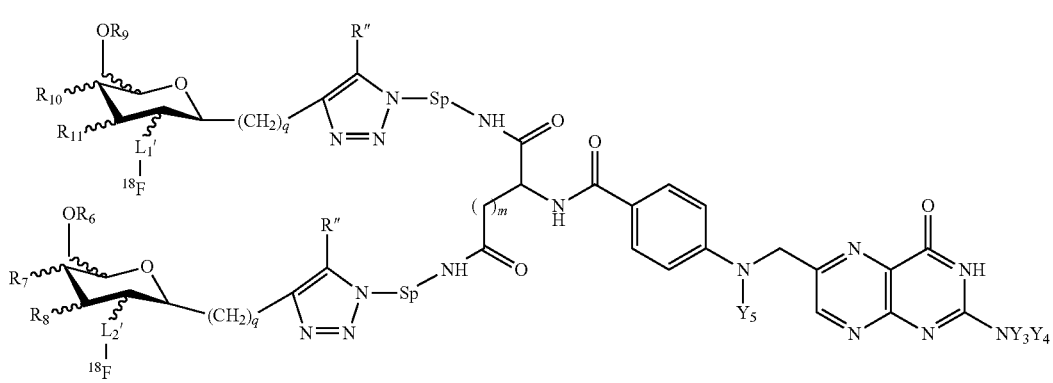
IXa
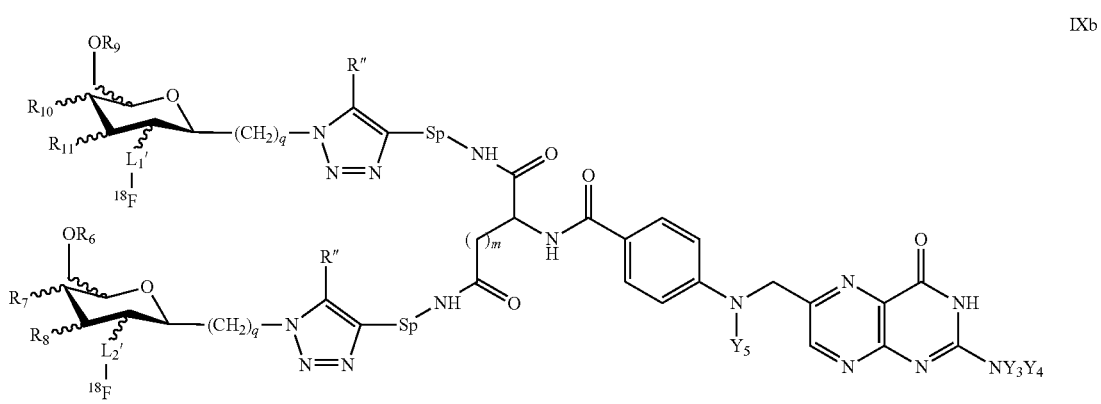
IXb
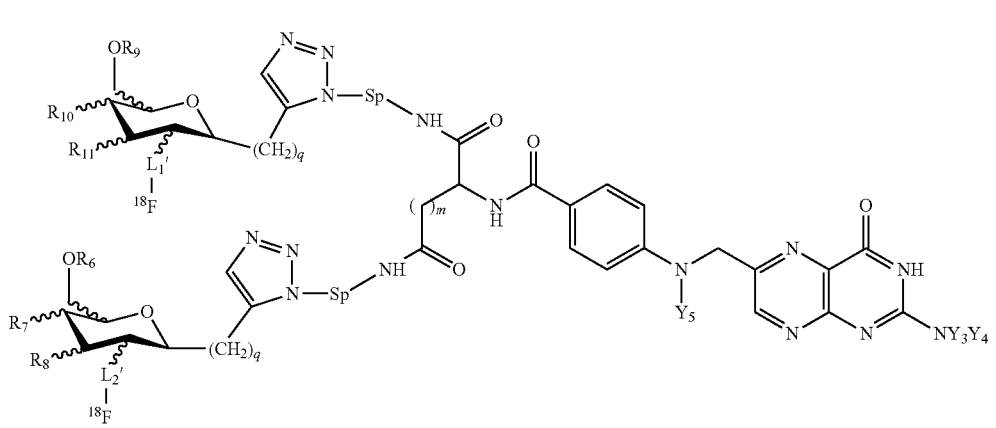
IXc

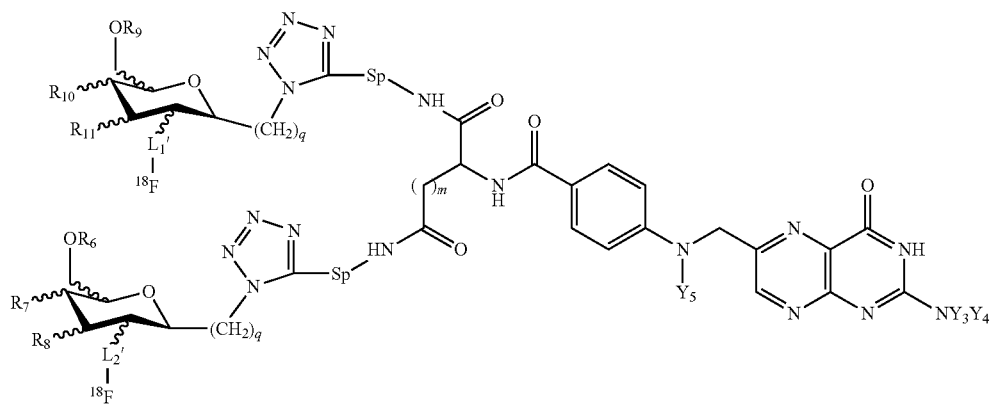

IXd wherein $Y_3, Y_4$ are independently of each other selected from H, halo, C(1-12)alkyl, C(2-12)alkenyl, C(2-12)alkynyl, —OR', —COR', —COOR', and —NHR', wherein R' is H or C(1-8)alkyl, $Y_5$ is selected from H, nitroso, C(1-12)alkyl, —OR', —COR', and halosubstituted —COR', wherein R' is H or C(1-12)alkyl, m is 1, 2 or 3, Sp are independently of each other a spacer such as a straight-chain or branched C(1-8)alkyl, which is unsubstituted or wherein at least one of the —$CH_2$— groups is substituted with —OH, —NHR', or —COOR', wherein R' represents H or C(1-8)alkyl, $L_1', L_2'$ are independently of each other a covalent bond or a straight-chain or branched C(1-6)alkyl, wherein one or more of the non-adjacent $CH_2$ groups may independently be replaced by a group selected from —O—, —CO—O—, —O—CO—, —NR'—, —NR'—CO—, —CO—NR', wherein R' represents H or C(1-8)alkyl, q is 0, 1, 2, 3 or 4, $R_6, R_9$ are independently of each other H or C(1-8)alkyl, and $R_7, R_8, R_{10}, R_{11}$ are independently of each other H, —OH, or —OC(1-8)alkyl.

In a further aspect the present invention also provides methods of synthesizing a compound of the invention. The synthesis is preferably based on a modular approach (using appropriately derivatized functionalities, i.e. folate group, saccharide group, etc.) and is based on various standard coupling chemistries known in the art, including esterification, amdiation, and the click-reaction (see also hereinabove). The latter reaction has been proven to be particularly useful and is based on the coupling of an azide and an alkyne group in a cycloaddition under thermal conditions or in the presence of a catalyst to obtain the final compound of choice (Kolb and Sharpless, Drug Discovery Today 2003, 8, 1128; Kolb et al. Angew. Chem. Int. Ed. 2001, 40, 2004; Rostovtsev, V. V. et al. Angew. Chem. Int. Ed. 2002, 41, 2596; US 2005/02222427; WO 06/116629). These reactions are known as Huisgen 1,3-dipolar cycloaddition (thermal conditions) and Click-Reaction (catalytic conditions) and have been described in the art (Kolb and Sharpless, Drug Discovery Today 2003, 8, 1128; Kolb et al. Angew. Chem. Int. Ed. 2001, 40, 2004; Rostovtsev et al. Angew. Chem. Int. Ed. 2002, 41, 2596; US 2005/02222427; WO 06/116629).

More specifically compounds of the present invention wherein the five membered heterocycle is a triazole may be obtained by cycloaddition of an azide $R_a$—$N_3$ with an alkyne $R_b$—C≡C—$R_c$ and compounds of formula I wherein the five-membered heterocycle is a tetrazole are obtained by cycloaddition of an azide $R_a$—$N_3$ with a cyanide $R_b$≡CN. All possible combinations are contemplated herein, i.e. $R_a$ being the folate derivative and $R_b$ being a saccharide group (or precursor thereof), as well as $R_b$ being the folate derivative and $R_a$ being a saccharide group (or precursor thereof). Thus the modular and versatile nature of the reaction allows to employ a wide variety of linkers to couple the radioisotope to folic acid.

It is also understood that the saccharide group may be substituted with the 18F isotope prior to coupling to the folate group or after coupling to the folate group.

It is also understood that one of the two coupling groups (i.e. the alkyne or azide group) may be specifically linked directly or through a linker to the α-carboxylic acid on the folate (under suitable protection of the γ-carboxylic acid) to obtain the α-regioisomer in pure form. Alternatively, one of the two coupling groups (i.e. the alkyne or azide group) may be specifically linked directly or through a linker to the γ-carboxylic acid on the folate (under suitable protection of the α-carboxylic acid) to obtain the γ-regioisomer in pure form.

It will be obvious for a skilled person to select appropriate conditions for the various coupling steps and choose appropriate protecting groups PG (e.g. see Greene & Wuts, Eds., Protective Groups in Organic Synthesis, 2nd Ed., 1991, John Wiley & Sons, NY.) and leaving groups LG (e.g. a halogen, tosylate, mesylate, triflate, carbonate group) to obtain the desired α- or γ-regioisomer.

In a further aspect the invention provides pharmaceutical compositions comprising a diagnostic imaging amount or a therapeutically effective amount of at least one compound of the present invention and a pharmaceutically acceptable carrier therefor. As used herein, a pharmaceutically acceptable carrier, which is present in an appropriate dosage, includes solvents, dispersion media, antibacterial and antifungal agents, isotonic agents, and the like which are physiologically acceptable. The use of such media and agents are well-known in the art.

In a further aspect the present invention provides uses of folate radiopharmaceuticals of the invention (which include compounds and pharmaceutical compositions of the invention) for convenient and effective administration to a subject in need for diagnostic imaging.

Thus the present invention provides a method for diagnostic imaging of a cell or population of cells expressing a folate-receptor, said method comprising the steps of administering at least one folate radiopharmaceutical of the invention in a diagnostic imaging amount, and obtaining a diagnostic image of said cell or population of cells.

Such imaging may be performed on a cell or population of cells expressing a folate-receptor in vitro or in vivo.

Thus, the present invention provides a method for in vitro detection of a cell expressing the folate receptor in a tissue sample which includes contacting said tissue sample with at least one folate radiopharmaceutical of the invention in effective amounts and for sufficient time and conditions to allow binding to occur and detecting such binding by PET imaging.

In a further aspect the present invention provides uses of folate radiopharmaceuticals of the present invention for convenient and effective administration to a subject in need for diagnostic imaging and/or monitoring of therapy of cancer and inflammatory and autoimmune diseases.

Thus, the present invention provides a method for simultaneous diagnosis and therapy, comprising the steps of administering to a subject in need thereof at least one folate radiopharmaceutical of the present invention in a diagnostically effective amount in combination with a therapeutically active compound of choice, and obtaining a diagnostic image of said tissues to follow the course of treatment.

The subject of the methods of the present invention is preferably a mammal, such as an animal or a human, preferably a human.

The dosage, i.e. diagnostically effective amount of the at least one folate radiopharmaceutical of the invention depends on the nature of the effect desired, such as the form of diagnosis, on the diagnostic instrumentation, on the form of application of the preparation, and on the age, weight, nutrition and condition of the recipient, kind of concurrent treatment, if any.

However, the most preferred dosage can be tailored to the individual subject, as is understood and determinable by one of skill in the art, without undue experimentation. This typically involves adjustment of a standard dose, e.g., reduction of the dose if the patient has a low body weight.

The imaging procedure in the PET scanner takes place from within minutes to 2-4 hours after administration of the radiotracer. The schedule depends on the imaging target and kinetics of the radiotracer as well as the desired information.

The preferred route of administration of the folate radiopharmaceuticals of the present invention is by intraveneous injection.

The suitable forms for injection include sterile aqueous solutions or dispersions of the above mentioned folate radiopharmaceuticals of the present invention. Typically the radiopharmaceutical will be formulated in physiological buffer solutions.

The folate radiopharmaceuticals can undergo sterilization by any art recognized technique, including but not limited to, addition of antibacterial of antifungal agents, for example, paraben, chlorobutanol, phenol, sorbic acid, thimerosal, and the like. Preferably they undergo a sterile filtration before administration eliminating the need of additional sterilisation agents.

For a solution to be injected a preferred unit dosage is from about 0.01 mL to about 10 mL. After intravenous administration, imaging of the organ or tumor in vivo can take place, if desired, from within minutes to 2-4 hours after the radiolabeled reagent has been administered to a subject to allow a sufficient amount of the administered dose to accumulate in the targeted area of choice.

The folate radiopharmaceuticals of the invention may also be used for in vitro detection of a cell expressing the folate receptor in a tissue biopsy taken from a subject. Thus in a further embodiment the present invention provides a method for in vitro detection of a cell expressing the folate receptor, e.g. a tumor cell, in a tissue sample which includes contacting said tissue sample with a folate radiopharmaceutical of the present invention in effective amounts and for sufficient time and conditions to allow binding to occur and detecting such binding by imaging techniques.

Samples can be collected by procedures known to the skilled person, e.g., by collecting a tissue biopsy or a body fluid, by aspirating for tracheal or pulmonary samples and the like.

Tissue samples to be tested include any arterial and vascular tissue including atherosclerotic plaque, suspected to contain a individual cell, groups of cells, or cell cultures, of a bodily tissue or fluid (e.g., blood cells) expressing a folate receptor, such as tumour cells, epithelial cells, kidneys, gastrointestinal or the hepatobiliary system, and others.

The tissue may be within a subject, or biopsied or removed from a subject. The tissue may also be a whole or any portion of a bodily organ. The tissue may be "fresh" in that the tissue would be recently removed from a subject without any preservation steps between the excision and the methods of the current invention. The tissue (samples) may also have been preserved by such standard tissue preparation techniques including, but not limited to, freezing, quick freezing, paraffin embedding and tissue fixation, prior to application of the methods of the current invention. Samples can be sectioned, e.g., with a microtome, to facilitate microscopic examination and observation. Samples can also be fixed with an appropriate fixative either before or after incubation with one of the folate radiopharmaceuticals of the present invention to improve the histological quality of sample tissues.

Time and conditions sufficient for binding of a folate radiopharmaceutical of the present invention to a folate receptor on the cell include standard tissue culture conditions, i.e. samples can be cultured in vitro and incubated with one of the compounds or compositions of the present invention in physiological media. Such conditions are well known to the skilled person. Alternatively, samples can be fixed and then incubated with a folate radiopharmaceutical of the present invention in an isotonic or physiological buffer.

For all applications it is convenient to prepare the compounds of the present invention at, or near, the site where they are to be used.

All of the compounds and/or methods disclosed and claimed herein can be made and executed without undue experimentation in light of the present disclosure. It will be apparent to those of skill in the art that variations may be applied to the present invention without departing from the scope of the invention. The Examples provided herein are intended to be illustrative and are not exhaustive; therefore the illustrated Examples should not be viewed as limiting the invention in any way.

EXAMPLES

Materials and Methods

Infrared spectra were recorded on a Jasco FT/IR-6200 ATR-IR. Nuclear magnetic resonance spectra were recorded with a Bruker 400 MHz or 500 MHz spectrometer with the corresponding solvent signals as an internal standard. Chemical shifts are reported in parts per million (ppm) relative to tetramethylsilane (0.00 ppm). Values of the coupling constant, J, are given in Hertz (Hz); the following abbreviations are used in the experimental section for the description of $^1$H-NMR spectra: singlet (s), doublet (d), triplet (t), multiplet (m), doublet of doublets (dd). The chemical shifts of complex multiplets are given as the range of their occurrence. Low resolution mass spectra (LR-MS) were recorded with a Micromass Quattro Micro™ API LC-ESI and high resolution mass spectra (HR-MS) with a Bruker FTMS 4.7 T BioAPEXII (ESI).

Reactions were monitored by thin layer chromatography (TLC, performed on EM Science 0.25 mm thick, precoated silica gel 60 F-254 glass supported plates) or HPLC. HPLC was performed on a Merck-Hitachi L-7000 system equipped with an L-7400 tunable absorption detector. Analytical HPLC was performed with a Gemini column (C18, 5 µm, 4.6×250 mm, Phenomenex) using the following solvent system (1 ml/min): 50 mM NH$_4$HCO$_3$ solution (solvent A), acetonitrile (solvent B); 0-4 min, 100% A; 4-5 min 100→93% A; 5-15 min 93% A; 15-25 min 93→30% A; 25-30 min 30% A; Semipreparative HPLC was performed with a Gemini column (C18, 5 µm, 10×250 mm, Phenomenex), 3 mL/min; with a solvent system and gradient as follows: 50 mM NH$_4$HCO$_3$ solution (solvent A) methanol (solvent B); 0-3 min 100% A; 3-28 min 100→40% A; 28-30 min 40→30% A; 30-35 min 30% A.

Analytical radio-HPLC was performed on a Merck-Hitachi L-2130 system equipped with a L-2450 diode array detector and a Berthold radio detector using the above mentioned column and gradient for the analytical HPLC.

For the in vitro stability studies, an ultra-performance liquid chromatography (UPLC™) system from Waters with a Waters Acquity UPLC BEH C18 column (2.1×50 mm, 1.7 µm) and an attached Berthold co-incidence detector (Flow-Star LB513) was used with the following gradient system: 50 mM NH$_4$HCO$_3$ solution (solvent A), acetonitrile (solvent B), 0.5 ml/min; 0-0.5 min 100% A; 0.5-3.5 min 100→30%; 3.5-3.9 min 30% A.

Semipreparative radio-HPLC purification of [$^{18}$F]glucose folic acid was carried out on a HPLC system equipped with a Merck-Hitachi L-6200A intelligent pump, a Knauer variable-wavelength ultraviolet detector and an Eberline RM-14 radiodetector using a Gemini column (C18, 5 µm, 250×10 mm, Phenomenex) and an isocratic solvent system of 50 mM NaH$_2$PO$_4$/Na$_2$HPO$_4$ buffer solution, adjusted to pH 7.0 and 5% ethanol at a flow rate of 3 ml/min.

All chemicals were used as supplied unlike stated otherwise. Production of n.c.a. [$^{18}$F]fluoride N.c.a. No-carrier-added [$^{18}$F]fluoride was produced via the $^{18}$O(p,n)$^{18}$F nuclear reaction at a Cyclone 18/9 cyclotron (IBA) by irradiation of enriched [$^{18}$O]water. [$^{18}$F]fluoride was immobilized on an anion-exchange cartridge (QMA Light; Waters; preconditioned with 0.5 M K$_2$CO$_3$-solution and H$_2$O) and eluted with a solution of Kryptofix K$_{222}$ (5 mg) and K$_2$CO$_3$ (1 mg) in acetonitrile (1.4 mL) and water (0.6 mL) into a 10 mL sealed reaction vessel. The fluoride was dried by azeotropic distillation of acetonitrile at 110° C. under vacuum with a stream of nitrogen. The azeotropic drying process was repeated 3 times with 1 mL of acetonitrile each time.

Example 1: Synthesis of γ-Folate Alkyne Precursor (According to FIG. 1A)

(a) Synthesis of (S)-methyl 2-((S)-4-((tert-butoxycarbonyl)-amino)-5-methoxy-5-oxopentananamido)pent-4-ynoate (Step a)

Commercial available BocGluOMe (402 mg, 1.54 mmol) was dissolved in dry DMF (4 mL) and Et$_3$N (428 µL, 2 eq.) was added. HBTU (700 mg, 1.85 mmol) was added at 0° C. and the mixture was stirred for half an hour. The solution of the activated acid was transferred to a solution of H-Pra-OMe.HCl (205 mg, 1.62 mmol) in dry DMF (4 mL) containing Et$_3$N (856 µL, 4 eq.) at 0° C. The mixture was stirred for 1 h at 0° C., warmed to rt and stirred over night. The product was extracted with citric acid (1 M) and ethyl acetate. The organic phase was rinsed with brine, dried over Na$_2$SO$_4$ and concentrated under reduced pressure. Purification was achieved by flash chromatography on silicagel with CH$_2$Cl$_2$/MeOH (50:1) provided the product as a white solid (467 mg, 82%). $^1$H-NMR (DMSO-d6) δ/ppm 8.40 (d, 1H, J=7.3 Hz), 7.27 (d, 1H, J=7.7 Hz), 4.45 (q, 1H, J=7.3 Hz), 4.00 (m, 1H), 3.68 (s, 3H), 3.66 (s, 3H), 2.92 (t, 1H, J=2.5 Hz), 2.62 (m, 2H), 2.26 (t, 2H, J=7.6 Hz), 2.04-1.71 (m, 2H), 1.42 (s, 9H); $^{13}$C-NMR (DMSO-d6) δ/ppm 173.8, 172.4, 171.8, 156.4, 80.9, 79.1, 74.1, 53.9, 53.0, 52.6, 51.9, 32.2, 29.1, 27.5, 21.9; HR-MS (ES$^+$) calculated for C$_{17}$H$_{27}$N$_2$O$_7$: 371.1813; found: 371.1816.

(b) Synthesis of (S)-methyl 2-((S)-4-amino-5-methoxy-5-oxopentananamido)pent-4-ynoate (Step b)

(S)-methyl 2-((S)-4-((tert-butoxycarbonyl)-amino)-5-methoxy-5-oxopentananamido)pent-4-ynoate (460 mg, 1.24 mmol) was dissolved in CH$_2$Cl$_2$ (4.5 mL) and trifluoroacetic acid (TFA; 0.5 mL) was added. The mixture was left at rt for 5 h and then concentrated under reduced pressure to yield the TFA salt of the amine as a yellow oil (332 mg, quantitative). $^1$H-NMR (DMSO-d6) δ/ppm 8.56 (d, 1H, J=7.3 Hz), 8.48 (bs, 1H), 4.46 (q, 1H, J=7.3 Hz), 4.10 (bs, 1H), 3.79 (s, 3H), 3.68 (s, 3H), 2.95 (t, 1H, J=2.6 Hz), 2.64 (m, 2H), 2.38 (m, 2H), 2.04 (m, 2H); $^{13}$C-NMR (DMSO-d6) δ/ppm 171.9, 171.7, 170.6, 81.0, 74.3, 53.8, 53.0, 52.5, 52.0, 31.1, 26.8, 21.9; HR-MS (ES$^+$) calculated for C$_{12}$H$_{19}$N$_2$O$_5$: 271.1288; found: 271.1298.

(c) Synthesis of γ-folate alkyne (Step c and d)

N$^2$—N,N-dimethylaminomethylene-10-formylpteoric acid (246 mg, 0.62 mmol) was suspended in dry DMF (2 mL) and Et$_3$N (165 µL, 2 eq.) was added. HBTU (314 mg, 0.83 mmol) was added at 0° C. and the suspension was stirred for 5 min until a clear orange solution appeared. The resulting solution was added at 0° C. to a solution of (S)-methyl 2-((S)-4-amino-5-methoxy-5-oxopentananamido)pent-4-ynoate (TFA salt; 160 mg, 0.59 mmol) in dry DMF (3 mL) containing Et$_3$N (165 µL, 2 eq.). The clear yellow solution was stirred at 0° C. for 4 h and then allowed to warm to rt and stirred 2 h. Removal of volatile components under reduced pressure and purification of the residue by flash chromatography on silicagel with CH$_2$Cl$_2$/MeOH (10:1) provided the protected γ-folate alkyne as a yellow solid (238 mg, 62%). LR-MS (ES+) calculated for $C_{30}H_{33}N_9O_8$: 647.25; found: 647.83.

NMR and HPLC indicated partial deprotection of the product, thus the compound was deprotected directly to yield the γ-folate alkyne precursor (see below).

Protected γ-folate alkyne (203 mg, 0.35 mmol) was dissolved in 1 M NaOH (6 mL) and stirred at rt over night. The aqueous solution was extracted with small amounts of ethyl acetate (3×1 ml) and afterwards the pH was adjusted to 8 with 2 M HCl. The solution was divided into two portions and the purification was achieved by two reversed-phase cartridges (Sep-Pak C18, 12 cc, 2 g; Waters; preconditioned with MeOH and $H_2O$). The cartridges were first washed with 3 ml $H_2O$ and then the product was eluted with 12 ml $H_2O$. After combining both product fractions and lyophilisation the γ-folate alkyne was obtained as a yellow powder (121 mg, 63%, purity according to HPLC>95%). $^1$H-NMR ($D_2O$/NaOD) δ/ppm 8.62 (s, 1H), 7.69 (d, 2H, J=8.8 Hz), 6.86 (d, 2H, J=8.8 Hz), 4.63 (s, 2H), 4.37 (q, 1H, J=4.5 Hz), 4.24 (t, 1H, J=5.7 Hz), 2.56 (m, 2H), 2.44 (m, 2H), 2.29 (m, 1H), 2.07 (m, 1H); HR-MS (ES+) calculated for $C_{24}H_{25}N_8O_2$: 537.1841; found: 537.1834.

Figure 2A:
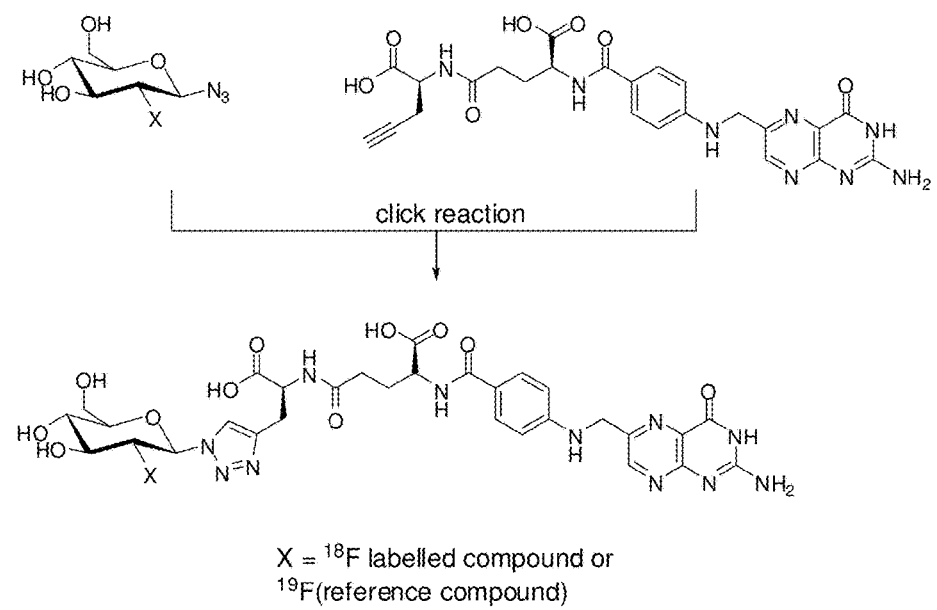
FIG. 2A: Synthesis scheme of the γ-regioisomer of [$^{18}$F]- or [$^{19}$F]-glucose folate compound.

Example 2: Synthesis of γ-[$^{19}$F]-Glucose Folate Reference (According to FIG. 2A)

The synthesis of 2-deoxy-2-fluoroglucopyranosyl azide was prepared according to the procedure according the literature procedure (e.g. Maschauer and Prante, Carbohydr. Res. 2009).

γ-Folate alkyne (10 mg, 19 µmol) was dissolved in tert-BuOH/$H_2O$ (1:1, 1 mL) in an Eppendorf tube and 2-deoxy-2-fluoroglucopyranosyl azide (11.6 mg, 56 µmol), 0.1 M $Cu(OAc)_2$ solution (0.1 eq., 19 µL) and 0.1 M sodium ascorbate solution (0.2 eq., 38 µL) were added. The solution was shaken at rt and 500 rpm for 1 h until complete conversion (analysis via HPLC). For isolation of the product, the mixture was submitted to semi-preparative HPLC. The desired fraction was collected and lyophilized to provide the product as a yellow powder (7.2 mg, 52%, purity according to HPLC>98%). $^1$H-NMR ($D_2O$/NaOD) δ/ppm 8.74 (s, 1H), 7.98 (s, 1H), 7.61 (d, 2H, J=8.8 Hz), 6.76 (d, 2H, J=8.8 Hz), 5.89 (dd, 1H, $J_1$=2.6 Hz, $J_2$=9.0 Hz), 4.91 (t, 1H, J=9.0 Hz), 4.61 (s, 2H), 4.44 (q, 1H, J=4.7 Hz), 4.35 (q, 1H, J=4.3 Hz), 4.02-3.86 (m, 2H), 3.79-3.62 (m, 2H), 3.20 (dd, 1H, $J_1$=4.7 Hz, $J_2$=14.8 Hz), 3.04 (dd, 1H, $J_1$=8.4 Hz, $J_2$=14.8 Hz), 2.37 (m, 2H), 2.17 (m, 1H), 2.01 (m, 1H); HR-MS (ES+) calculated for $C_{30}H_{35}FN_{11}O_{11}$: 744.2496; found: 744.2508.

Example 3: Synthesis of γ-[$^{18}$F]-glucose folate (according to FIG. 2A)

The 3,4,6-tri-O-acetyl-2-O-trifluoromethanesulfonyl-β-D-mannopyranosyl azide precursor used for coupling the $^{18}$F-substituted glucose via click reaction to the folate, was obtained according to literature procedures (e.g. Maschauer and Prante, Carbohydr. Res. 2009, 753; Takatani et al Carbohydr. Res. 2003, 1073).

(b) Radiosynthesis of 2-[$^{18}$F]fluoroglucopyranosyl azide

To the dry $^{18}$F-fluoride-cryptate complex the precursor, 3,4,6-tri-O-acetyl-2-O-trifluoromethanesulfonyl-β-D-mannopyranosyl azide (3.0 mg, 6.5 µmol), in 0.30 mL of anhydrous acetonitrile was added. The mixture was stirred for 5 min at 80° C. to afford a $^{18}$F-incorporation of maximum 75% according to radio-UPLC analysis. After 5 min of cooling and addition of 8 mL of water, the mixture was passed through a reversed-phase cartridge (Sep-Pak C18 Plus; Waters; preconditioned with MeOH and $H_2O$). The cartridge was washed with 5 mL of water. The $^{18}$F-labelled protected intermediate, 3,4,6-tri-O-acetyl-2-deoxy-2-[$^{18}$F] fluoroglucopyranosyl azide, was eluted with 2.0 mL of acetonitrile into another 10 mL sealed reaction vessel and dried under reduced pressure and a nitrogen stream at 80° C. For hydrolysis, 0.25 mL of 60 mM sodium hydroxide solution was added and the mixture was heated to 65° C. for 5 min to complete the deacetylation. After cooling, the mixture was neutralized with 0.25 mL of 60 mM hydrogen chloride solution and directly used for the click reaction without further purification.

(c) Coupling to γ-Folate Alkyne Precursor

The deprotected 2-deoxy-2-[$^{18}$F]fluoroglucopyranosyl azide obtained in step (b) was transferred into another reaction vessel containing the γ-folate alkyne, followed by addition of 0.3 mL ethanol, 10 µL 0.1 M $Cu(OAc)_2$ solution and 20 µL 0.1 M sodium ascorbate solution. The reaction mixture was stirred at 50° C. for 15 min. After addition of 3 mL of 0.15 M phosphate buffer solution the mixture was submitted to the semipreparative radio-HPLC system. The product fraction γ-[$^{18}$F]-glucose folate was passed through a sterile filter and collected into a sterile, pyrogen-free vial without further formulation. The overall decay-corrected yield of the isolated product reached 25% after a total synthesis time of 3 h with a radiochemical purity always greater than 95%. The specific activity of γ-[$^{18}$F]-glucose folate was up to 120 GBq/µmol.

Figure 1B:
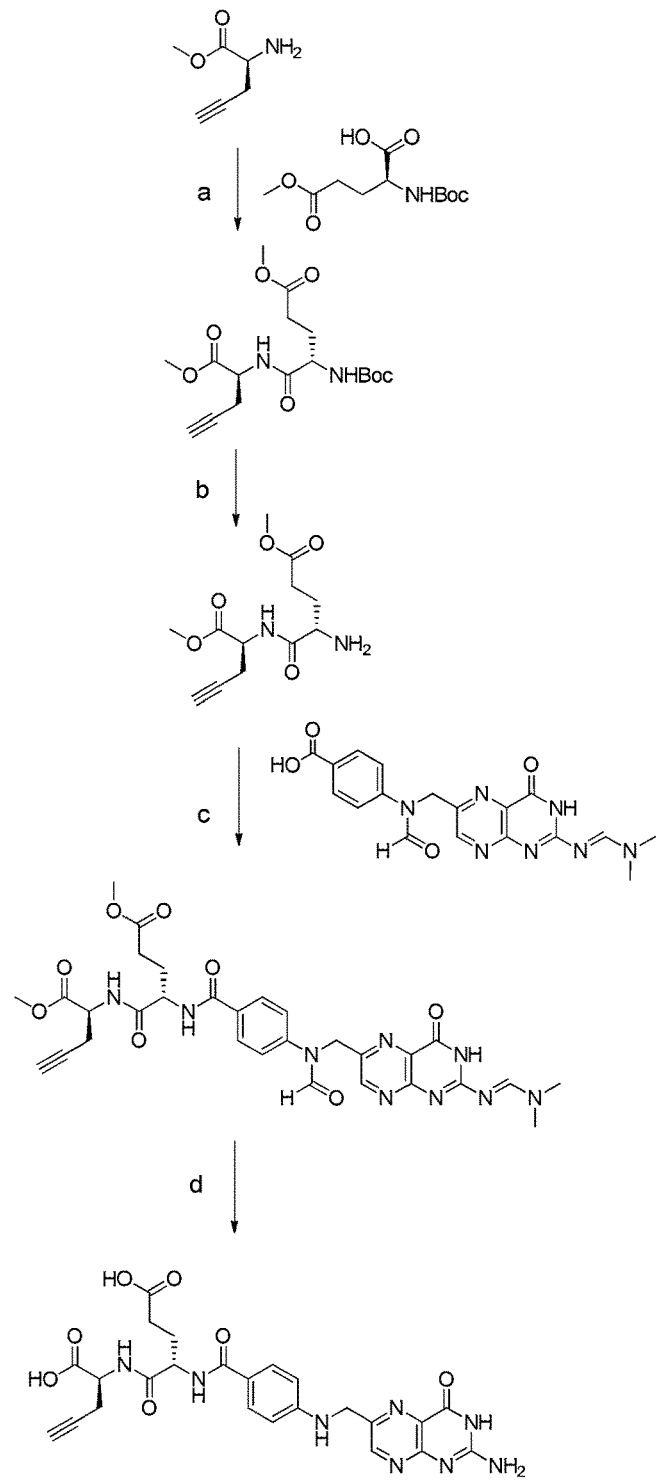
FIG. 1B: Synthesis scheme of α-folate alkyne precursor.

Example 4: Synthesis of α-Folate Alkyne Precursor (According to FIG. 1B)

(a) Synthesis of (S)-methyl 2-((S)-2-((tert-butoxycarbonyl)-amino)-5-methoxy-5-oxopentanamido)pent-4-ynoate The alkyne was prepared in analogy to Example 1 using BocGluOMe-OH.DCH as the starting material. The product of step a occurred as a clear oil (326 mg, 80%). $^1$H-NMR (DMSO-d6) δ/ppm 8.34 (d, 1H, J=7.8 Hz), 6.97 (d, 1H, J=8.4 Hz), 4.46 (m, 1H), 4.05 (m, 1H), 3.68 (s, 3H), 3.62 (s, 3H), 2.94 (t, 1H, J=2.6 Hz), 2.66 (dd, 2H, $J_1$=2.6 Hz, $J_2$=6.8 Hz), 2.38 (m, 2H), 2.00-1.71 (m, 2H), 1.42 (s, 9H); $^{13}$C-NMR (DMSO-d6) δ/ppm 173.8, 172.7, 171.6, 156.1, 80.7, 79.1, 74.4, 54.1, 53.1, 52.3, 51.8, 30.7, 29.1, 28.2, 21.8; HR-MS (ES+) calculated for $C_{17}H_{26}N_2NaO_7$: 393.1632; found: 393.1641.

(b) Synthesis of (S)-methyl 2-((S)-2-amino-5-methoxy-5-oxopentanamido)pent-4-ynoate (Step b)

(S)-methyl 2-((S)-2-((tert-butoxycarbonyl)-amino)-5-methoxy-5-oxopentanamido)pent-4-ynoate (270 mg, 0.73 mmol) was dissolved in $CH_2Cl_2$ (4.5 mL) and trifluoroacetic acid (TFA; 0.5 mL) was added. The mixture was left at rt for 5 h and then concentrated under reduced pressure to yield the TFA salt of the amine as a yellow oil (198 mg, quantitative). $^1$H-NMR (DMSO-d6) δ/ppm 9.12 (d, 1H, J=7.4 Hz), 8.28 (bs, 2H), 4.54 (m, 1H), 3.99 (m, 1H), 3.70 (s, 3H), 3.65 (s, 3H), 3.04 (t, 1H, J=2.7 Hz), 2.72 (m, 2H), 2.49 (m, 2H), 2.05 (m, 2H); $^{13}$C-NMR (DMSO-d6) δ/ppm 173.2, 171.1, 169.4, 80.5, 74.8, 53.3, 52.5, 52.2, 52.1, 29.4, 27.2, 21.6; HR-MS (ES$^+$) calculated for $C_{12}H_{19}N_2O_5$: 271.1288; found: 271.1291.

(c) Synthesis of α-Folate Alkyne $N^2$—N,N-dimethylaminomethylene-10-formylpteoric acid (246 mg, 0.62 mmol) was suspended in dry DMF (2 mL) and Et$_3$N (165 μL, 2 eq.) was added. HBTU (314 mg, 0.83 mmol) was added at 0° C. and the suspension was stirred for 5 min until a clear orange solution appeared. The resulting solution was added at 0° C. to a solution of (S)-methyl 2-((S)-2-amino-5-methoxy-5-oxopentanamido) pent-4-ynoate (TFA salt; 160 mg, 0.59 mmol) obtained in according to Example 1(b) in dry DMF (3 mL) containing Et$_3$N (165 μL, 2 eq.).

The clear yellow solution was stirred at 0° C. for 4 h and then allowed to warm to rt and stirred overnight. Removal of volatile components under reduced pressure and purification of the residue by flash chromatography on silicagel with CH$_2$Cl$_2$/MeOH (10:1) provided the protected α-folate alkyne as a yellow solid. LR-MS [M+H]$^+$: 648.12.

NMR and HPLC indicated partial deprotection of the product, thus the compound was deprotected directly to yield the α-folate alkyne using the procedure described below.

Protected α-folate alkyne was dissolved in 1 M NaOH (6 mL) and stirred overnight at rt. The aqueous solution was extracted with small amounts of ethyl acetate (3×1 mL) and afterwards the pH was adjusted to 8 with 2 M HCl (30 μL). The solution was diluted with 50 mM NH$_4$HCO$_3$ solution (5 ml) and submitted to preparative HPLC. The desired fraction was collected and lyophilized to provided product α-folate alkyne as a yellow powder (84 mg, 26% over 2 steps, purity according to HPLC>98%). $^1$H-NMR (D$_2$O/NaOD) δ/ppm 8.58 (s, 1H), 7.67 (d, 2H, J=8.5 Hz), 6.81 (d, 2H, J=9.8 Hz), 4.58 (s, 2H), 4.46 (q, 1H, J=4.8 Hz), 4.31 (t, 1H, J=5.9 Hz), 2.68 (m, 2H), 2.33 (t, 2H, J=7.7 Hz), 2.16 (m, 1H), 2.05 (m, 1H); HR-MS (ES$^+$) calculated for $C_{24}H_{24}N_8NaO_7$: 559.1660; found: 559.1659.

Figure 2B:
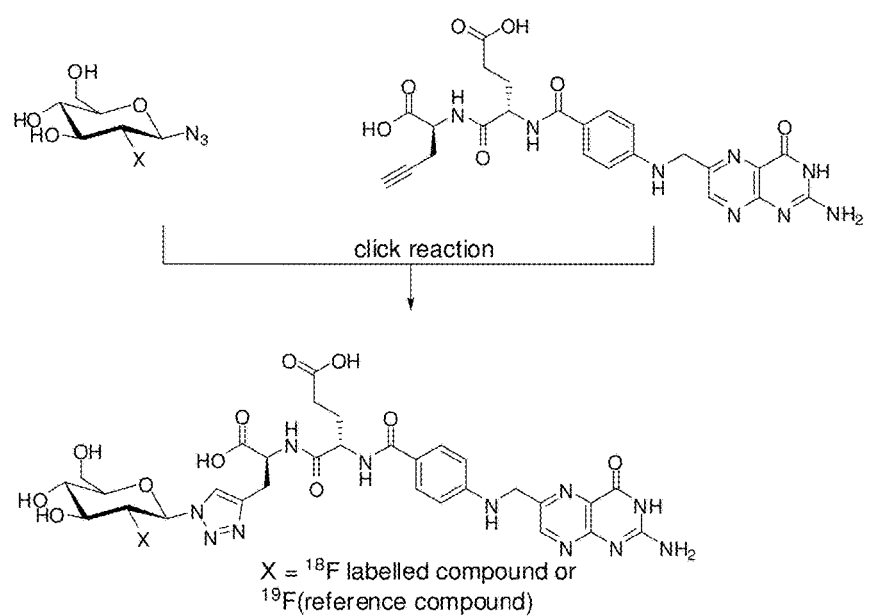
FIG. 2B: Synthesis scheme of the α-regioisomer of [$^{18}$F]- or [$^{19}$F]-glucose folate compound.

Example 5: Synthesis of α-[$^{19}$F]-Glucose Folate Reference (According to FIG. 2B)

The synthesis of 2-deoxy-2-fluoroglucopyranosyl azide was prepared according to the procedure according the literature procedure (e.g. Maschauer and Prante, Carbohydr. Res. 2009) α-Folate alkyne (10 mg, 19 μmol) was dissolved in tert-BuOH/H$_2$O (1:1, 1 mL) in an Eppendorf tube and 2-deoxy-2-fluoroglucopyranosyl azide (11.6 mg, 56 μmol), 0.1 M Cu(OAc)$_2$ solution (0.1 eq., 19 μL) and 0.1 M sodium ascorbate solution (0.2 eq., 38 μL) were added. The solution was shaken at rt and 500 rpm for 1 h until complete conversion (analysis via HPLC). For isolation of the product, the mixture was submitted to semi-preparative HPLC. The desired fraction was collected and lyophilized to provided product as a yellow powder (7.2 mg, 52%, purity according to HPLC>98%). $^1$H-NMR (D$_2$O/NaOD) δ/ppm 8.74 (s, 1H), 7.98 (s, 1H), 7.61 (d, 2H, J=8.8 Hz), 6.76 (d, 2H, J=8.8 Hz), 5.89 (dd, 1H, J$_1$=2.6 Hz, J$_2$=9.0 Hz), 4.91 (t, 1H, J=9.0 Hz), 4.61 (s, 2H), 4.44 (q, 1H, J=4.7 Hz), 4.35 (q, 1H, J=4.3 Hz), 4.02-3.86 (m, 2H), 3.79-3.62 (m, 2H), 3.20 (dd, 1H, J$_1$=4.7 Hz, J$_2$=14.8 Hz), 3.04 (dd, 1H, J$_1$=8.4 Hz, J$_2$=14.8 Hz), 2.37 (m, 2H), 2.17 (m, 1H), 2.01 (m, 1H); HR-MS (ES$^+$) calculated for $C_{30}H_{35}FN_{11}O_{11}$: 744.2496; found: 744.2508.

Example 6: Synthesis of α-[$^{18}$F]-Glucose Folate (According to FIG. 2B)

The radiosynthesis of α-[$^{18}$F]-glucose folate was performed in the same way as the radiosynthesis of the gamma-regioisomer. The overall decay-corrected yield of the isolated product was 3-10% after a total synthesis time of 3 h with a radiochemical purity always greater than 95%. The specific activity of [$^{18}$F]-glucose alpha-folate was up to 110±30 GBq/μmol.

Example 7: In Vitro Binding Affinity Assays

Binding affinity assays were performed with KB cells derived from human cervical carcinoma, where the folate receptor is overexpressed. The cells were cultured as monolayers in 75 cm$^2$ flasks at 37° C. in a humidified atmosphere (7.5% CO$_2$). The cells were kept in a special folate-deficient RPMI 1640 medium (FFRPMI 1640; Cell Culture Technologies) supplemented with heat-inactivated fetal calf serum (10%), L-glutamine, penicillin (100 IU/mL), and streptomycin (100 mg/mL). The fetal calf serum was the only source of folate in the medium, which is reported to provide a final folate concentration of about 3 nmol/mL, which is at the low end of the physiologic serum concentration in humans.

A cell suspension in pure FFRPMI 1640 medium (no additives, ice-cold) was added into 1.5 mL vials (7000 cells in 240 μL). The cells were incubated in triplicates with $^3$H-folic acid (0.82 nM) and increasing concentrations of the non-radioactive reference compound glucose folate 3 (5.0×10$^{-7}$ to 5.0×10$^{-12}$ M) at 4° C. for 30 min. Non-specific binding was determined in the presence of an excess of folic acid (10$^{-3}$ M). After incubation, the suspension was centrifuged at 3500 rpm and 4° C. for 5 min and the supernatant was removed. By addition of 0.5 mL of 1 N NaOH, the cell pellets were resuspended and lysed at the same time. The lysed cells were stirred in a vortex mixer and transferred into scintillation tubes containing 4 mL of scintillation cocktail (Ultima Gold; Perkin Elmer). Radioactivity was measured using a β-counter (LS6500; Beckman), and the inhibitory concentrations of 50% were determined from displacement curves using Graph Pad Prism 4.0 software.

Figure 3:
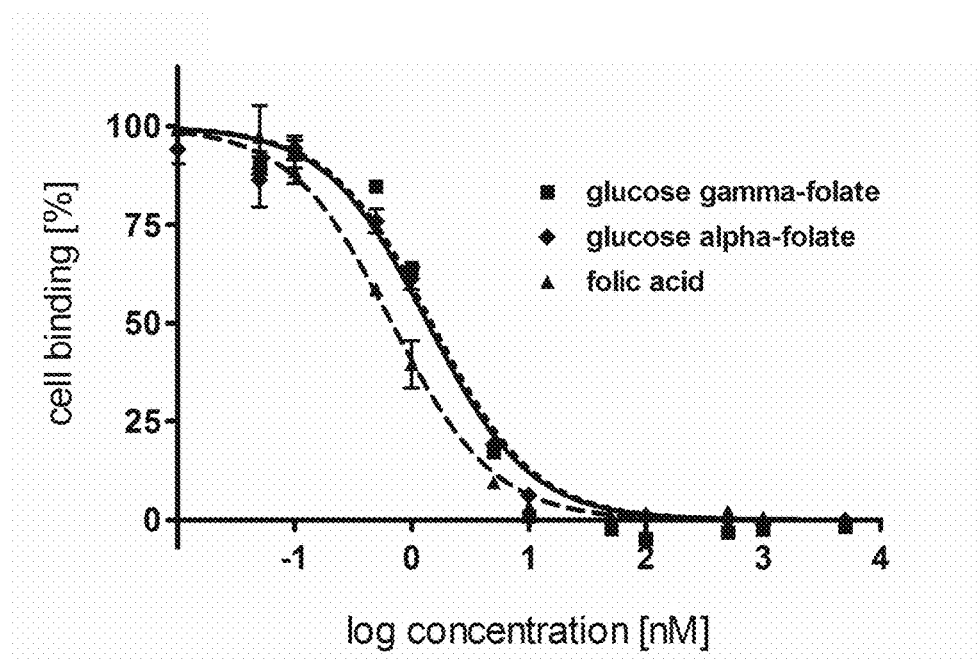
FIG. 3: Displacement curves of the two regioisomers α-glucose folate and γ-glucose folate and folic acid (squares represent γ-[[18]F-]-glucose folate, diamonds represent α-[$^{18}$F]-glucose folate, triangles represent folic acid).

The mean inhibitory concentration of 50% (IC$_{50}$ value) for glucose folate was obtained from three independent experiments and was found to be 1.6±0.1 nM (K$_i$=0.8±0.1 nM) for the γ-regioisomer and 1.4±0.2 nM (K$_i$=0.7±0.2 nM) for the α-regioisomer compare to folic acid, which shows a value of 0.8±0.2 nM (K$_i$=0.4±0.1 nM). The displacement curves of one experiment are outlined in FIG. 3 (squares indicate γ-glucose folate, rhombus indicate α-glucose folate, triangles indicate folic acid).

Example 8: In Vitro Stability Studies

The stability of γ-[$^{18}$F]-glucose folate was investigated in human plasma at various incubation times (0-120 min) at 37° C. After incubation, plasma proteins were precipitated with ice-cold methanol and centrifuged for 10 min at 13500 rpm and 20° C. The PBS control was diluted with the same volume of methanol. The supernatants and the PBS control were analyzed by analytical radio-UPLC. Both regioisomers of [$^{18}$]-glucose folate did not show any degradation products in human plasma for up to 120 min.

Example 9: Determination of Distribution Coefficient

The distribution coefficient (log D$_{7.4}$) was determined by the shake flask method. In brief, γ-[$^{18}$F]-glucose folate was dissolved in a mixture of phosphate buffer (500 µL, pH 7.4) and n-octanol (500 mL) at 20° C. The sample was equilibrated for 15 min in an over-head shaker. The two phases were separated by centrifugation (3 min, 5000 rpm) and 50 µL aliquots were taken from each layer and counted for radioactivity in a γ-counter. The partition coefficient is expressed as the ratio of radioactivity (cpm) in the octanol phase to the one in the PBS phase represents the mean±standard deviation of eight measurements.

The log $D_{7.4}$ values of both regioisomers of [$^{18}$F]-glucose folate were found to be −4.21±0.14 for the γ-regioisomer and −4.20±0.06 for the α-regioisomer (indicating the increased hydrophilicity of the compound).

Example 10: Biodistribution Studies

Figure 4A:
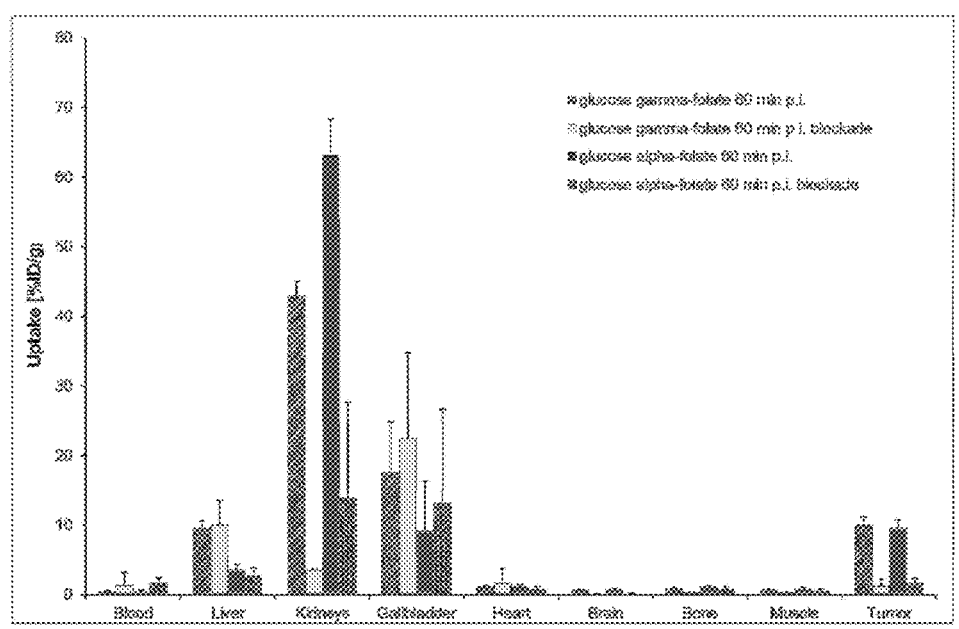
FIG. 4A: Comparison of biodistribution data between the α-[$^{18}$F]-glucose folate and γ-[$^{18}$F]-glucose folate 60 min p.i.
Figure 4B:
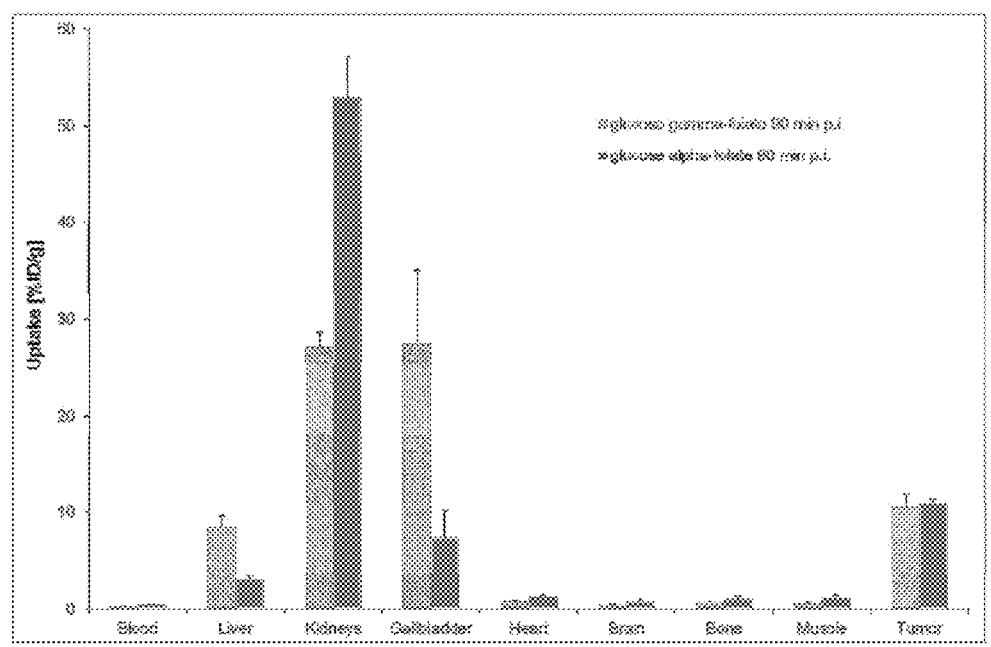
FIG. 4B: Comparison of biodistribution data between the α-[$^{18}$F]-glucose folate and γ-[$^{18}$F]-glucose folate 90 min p.i.

Female CD-1 nude mice were purchased from Charles River (Germany) and maintained on a folate-deficient rodent diet to reduce their serum folate concentration to a level comparable to human serum levels. After a 3-4 day acclimatization period, 0.1 mL of a KB tumor cell suspension (5×10$^6$ cells) was inoculated subcutaneously into both axilla of each mouse. The animal experiments were performed days after inoculation. Animals were injected with ~5 MBq, (max. volume 100 µL per injection) of γ-[$^{18}$F]-glucose folate via a lateral tail vein. Blocking studies (n=2) were performed with excess is acid dissolved in PBS (100 µg/100 µl) which was intravenously injected 10 min before the radiotracer. Animals were sacrificed at three different timepoints (30 min, 60 min, 90 min) after radiotracer injection. Organs- and tissues were dissected and measured in the γ-counter (Wizard, PerkinElmer). The incorporated radioactivity was expressed as percentage injected dose (% ID) per gram of tissue. The biodistribution data taken at various timepoints is summarized in Table 1 for the γ-regioisomer and in Table 2 for the α-regioisomer of [$^{18}$F]-glucose folate. In the blockade group (last column in the table) each animal received 100 µg/100 µL of folic acid in PBS 10 min before radiotracer injection. FIG. 4A illustrates the comparison in the biodistribution between the γ- and α-regioisomer at 60 min p.i. for different tissues (striped column: γ-regioisomer, empty column: γ-regioisomer blockade group, filled column: α-regioisomer, dotted column: α-regioisomer blockade group). FIG. 4B illustrates the comparison in the biodistribution between the γ- and α-regioisomer at 90 min p.i. for different tissues (dotted grey column: γ-regioisomer, filled black column: α-regioisomer).

TABLE 1

Ex vivo biodistribution studies with γ-[$^{18}$F]-glucose folate in nude mice bearing KB tumor xenografts at various time points

| Organ or tissue | 30 min p.i. (n = 4) | 60 min p.i. (n = 4) | 90 min p.i. (n = 4) | 60 min p.i. blockade (n = 2) |
|---|---|---|---|---|
| % ID/g in: | | | | |
| Spleen | 0.61 ± 0.13 | 0.73 ± 0.21 | 0.60 ± 0.22 | 0.23 ± 0.05 |
| Liver | 10.82 ± 1.68 | 9.49 ± 1.13 | 8.37 ± 1.19 | 10.00 ± 3.53 |
| Kidneys | 32.44 ± 1.84 | 42.94 ± 2.04 | 27.08 ± 1.53 | 3.48 ± 0.14 |
| Lungs | 1.18 ± 0.14 | 0.92 ± 0.07 | 0.71 ± 0.12 | 0.46 ± 0.06 |
| Bone | 0.90 ± 0.13 | 0.87 ± 0.05 | 0.72 ± 0.04 | 0.29 ± 0.01 |
| Heart | 1.04 ± 0.14 | 1.15 ± 0.13 | 0.81 ± 0.01 | 1.66 ± 2.05 |
| Brain | 0.38 ± 0.06 | 0.59 ± 0.08 | 0.45 ± 0.07 | 0.04 ± 0.02 |
| Gallbladder | 9.53 ± 6.01 | 17.59 ± 7.22 | 27.42 ± 7.57 | 22.49 ± 12.25 |
| Tumor | 9.61 ± 1.73 | 10.03 ± 1.12 | 9.05 ± 2.12 | 1.19 ± 1.04 |
| Blood | 0.94 ± 0.31 | 0.44 ± 0.09 | 0.25 ± 0.08 | 1.37 ± 1.80 |
| Urine | 531.51 ± 240.19 | 169.96 ± 151.53 | 134.12 ± 77.15 | 973.44 ± 1097.77 |
| Stomach | 1.27 ± 0.20 | 1.42 ± 0.53 | 1.03 ± 0.01 | 0.33 ± 0.08 |
| Intestine | 1.48 ± 0.46 | 3.45 ± 1.61 | 3.69 ± 0.04 | 4.56 ± 2.05 |
| Feces | 6.56 ± 4.41 | 10.95 ± 4.33 | 18.40 ± 6.83 | 20.48 ± 0.21 |
| Muscle | 0.89 ± 0.15 | 0.69 ± 0.05 | 0.57 ± 0.12 | 0.26 ± 0.04 |
| Salivary glands | 4.61 ± 0.44 | 5.93 ± 0.77 | 4.90 ± 0.01 | 0.30 ± 0.01 |
| Ratio of tumor to: | | | | |
| Liver | 0.89 ± 0.14 | 1.06 ± 0.02 | 1.28 ± 0.22 | 0.15 ± 0.16 |
| Kidneys | 0.29 ± 0.04 | 0.23 ± 0.04 | 0.34 ± 0.07 | 0.33 ± 0.28 |
| Blood | 10.57 ± 1.65 | 24.10 ± 7.44 | 36.09 ± 15.37 | 10.61 ± 14.77 |

TABLE 2

Ex vivo biodistribution studies with α-[$^{18}$F]-glucose folate in nude mice bearing KB tumor xenografts at various time points

| Organ or tissue | 30 min p.i. (n = 4) | 60 min p.i. (n = 4) | 90 min p.i. (n = 4) | 120 min p.i. (n = 4) | 60 min p.i. blockade (n = 2) |
|---|---|---|---|---|---|
| % ID/g in: | | | | | |
| Spleen | 0.94 ± 0.15 | 0.69 ± 0.08 | 0.70 ± 0.17 | 00.66 ± 0.11 | 0.46 ± 0.19 |
| Liver | 7.84 ± 1.05 | 3.55 ± 0.74 | 3.01 ± 0.48 | 2.55 ± 0.20 | 2.75 ± 1.01 |

TABLE 2-continued

Ex vivo biodistribution studies with α-[$^{18}$F]-glucose folate
in nude mice bearing KB tumor xenografts at various time points

| Organ or tissue | 30 min p.i. (n = 4) | 60 min p.i. (n = 4) | 90 min p.i. (n = 4) | 120 min p.i. (n = 4) | 60 min p.i. blockade (n = 2) |
|---|---|---|---|---|---|
| Kidneys | 85.77 ± 8.06 | 63.12 ± 5.14 | 52.91 ± 4.20 | 43.82 ± 3.12 | 13.88 ± 13.78 |
| Lungs | 1.88 ± 0.14 | 1.17 ± 0.04 | 1.17 ± 0.23 | 0.95 ± 0.12 | 1.28 ± 0.59 |
| Bone | 1.54 ± 0.09 | 1.15 ± 0.05 | 1.05 ± 0.33 | 0.90 ± 0.15 | 0.72 ± 0.38 |
| Heart | 1.75 ± 0.15 | 1.33 ± 0.08 | 1.26 ± 0.15 | 1.17 ± 0.11 | 0.74 ± 0.36 |
| Brain | 0.74 ± 0.18 | 0.76 ± 0.08 | 0.80 ± 0.16 | 0.99 ± 0.31 | 0.08 ± 0.04 |
| Gallbladder | 7.70 ± 2.12 | 9.09 ± 7.28 | 7.45 ± 2.65 | 9.59 ± 6.90 | 13.07 ± 13.66 |
| Tumor | 9.22 ± 0.30 | 9.55 ± 1.14 | 10.88 ± 0.52 | 11.17 ± 0.58 | 1.69 ± 0.59 |
| Blood | 0.92 ± 0.12 | 0.52 ± 0.07 | 0.41 ± 0.02 | 0.33 ± 0.08 | 1.66 ± 0.72 |
| Stomach | 2.11 ± 0. | 1.53 ± 0.29 | 1.56 ± 0.29 | 1.54 ± 0.18 | 0.66 ± 0.35 |
| Intestine | 1.45 ± 0.24 | 1.10 ± 0.29 | 0.86 ± 0.25 | 1.50 ± 1.18 | 2.53 ± 2.25 |
| Feces | 3.48 ± 1.03 | 5.44 ± 3.48 | 2.58 ± 0.34 | 5.04 ± 2.56 | 10.91 ± 7.80 |
| Muscle | 1.79 ± 0.75 | 0.89 ± 0.18 | 1.15 ± 0.25 | 1.11 ± 0.36 | 0.55 ± 0.24 |
| Salivary glands | 10.14 ± 2.13 | 7.19 ± 1.27 | 7.12 ± 1.75 | 6.11 ± 1.18 | 0.61 ± 0.28 |
| Ratio of tumor to: | | | | | |
| Liver | 1.19 ± 0.19 | 2.73 ± 0.30 | 3.73 ± 0.88 | 4.38 ± 0.15 | 0.62 ± 0.08 |
| Kidneys | 0.11 ± 0.01 | 0.15 ± 0.02 | 0.21 ± 0.03 | 0.26 ± 0.01 | 0.19 ± 0.11 |
| Blood | 10.23 ± 1.72 | 18.86 ± 4.55 | 26.49 ± 1.85 | 35.36 ± 7.30 | 1.06 ± 0.14 |

Example 11: PET Imaging Studies

PET experiments were performed with Explore VISTA PET/CT tomograph (GE), which provides an ultrahigh resolution of less than 0.9 mm.

Animals were lightly restrained and injected with 10-14 MBq of γ-[$^{18}$F]-glucose folate (100-150 μL per injection) via a lateral tail vein. For blocking studies, the animal received excess folic acid dissolved in PBS (100 μg/100 μL) via intravenous injection 10 min prior to the radiotracer injection. Animals were anesthetized with isoflurane in an air/oxygen mixture. The PET scans were acquired from 75-105 min post-injection. The fused datasets of PET and CT were analyzed with Amira (Version 4) postprocessing software.

Figure 5:
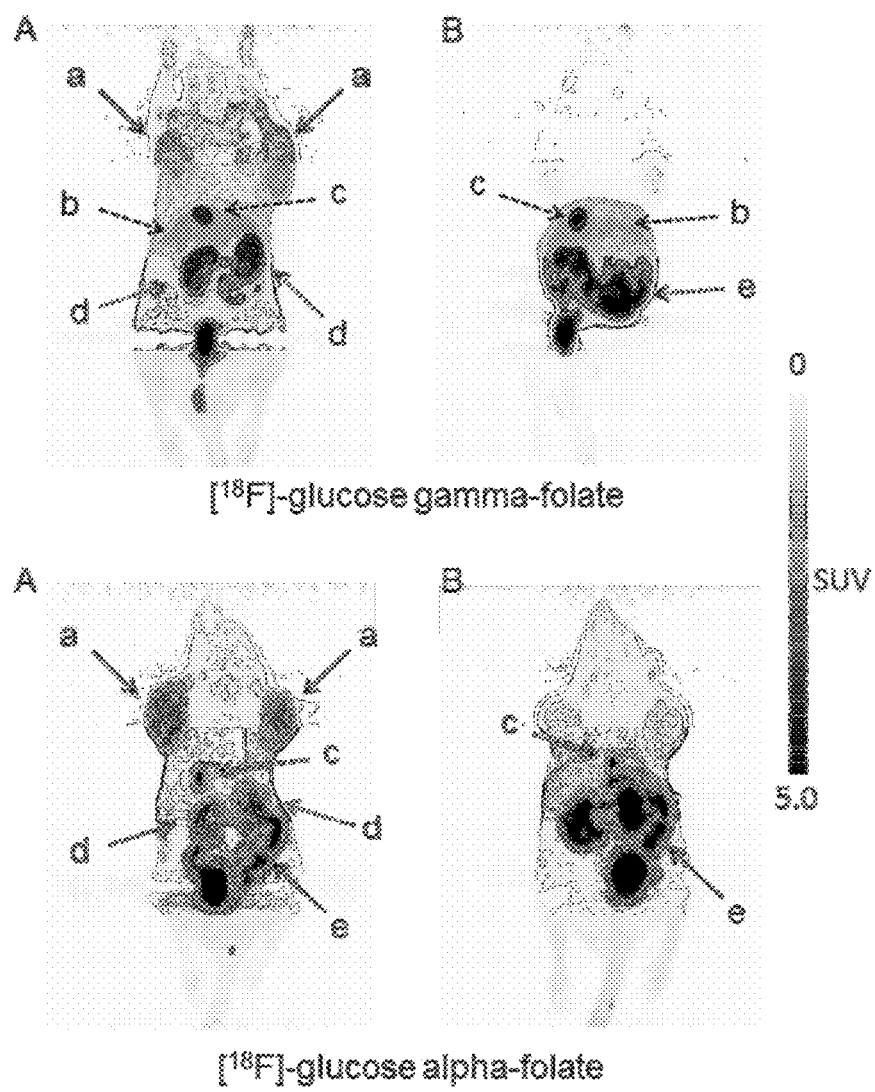
FIG. 5: Maximal intensity PET images of α-[$^{18}$F]-glucose folate and γ-[$^{18}$F]-glucose folate at time point 75-105 min p.i with (a): tumor, (b): liver, (c): gallbladder, (d): kidneys, (e): intestines/feces.

PET studies using the γ- and α-regioisomer of [$^{18}$F]-glucose folate provided excellent images of KB tumor xenografts on both shoulders. Furthermore the uptake is highly specific and blocked by natural folic acid. FIGS. 5A,B show PET images of both isomers at time point 75-105 min p.i. FIG. 5B are PET images of the blockade group. The symbols indicate the following organs/tissues: (a): tumor, (b): liver, (c): gallbladder, (d): kidneys, (e): intestines/feces.

The invention claimed is:
1. A compound of one of formulae Va, Vb or Vc:

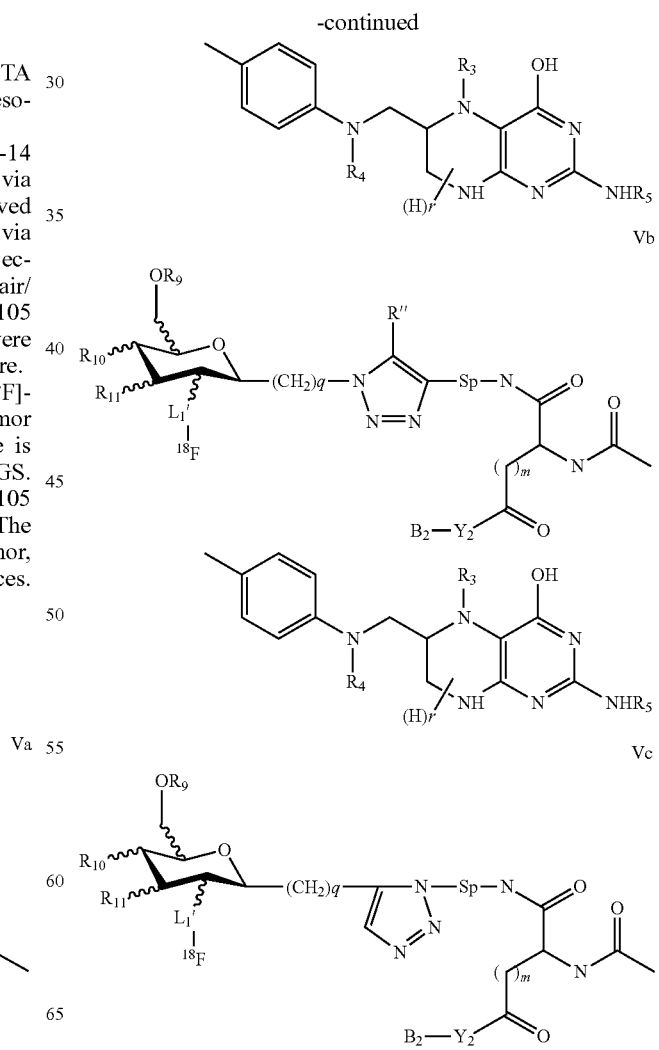

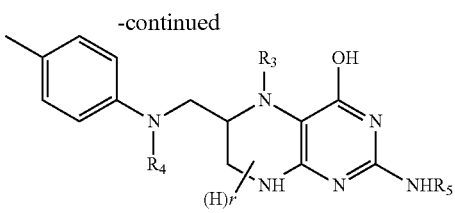

including tautomer, enantiomer and racemate forms thereof,
wherein
$R_5$ represents H or C(1-4)alkyl
$R_3$ and $R_4$ are, independently of each other: H, C(1-4)alkyl or —COR',
R' represents H or C(1-4)alkyl,
m is 1, 2 or 3,
r has a value of 1 to 7,
$Y_2$ is O, N or S,
$B_2$ is H, or a protecting group,
R" is H or a straight-chain or branched C(1-8)alkyl, which is unsubstituted or substituted by at least one CN, Hal, or $NO_2$,
Sp is a spacer which is a straight-chain or branched C(1-8)alkyl, which is unsubstituted or wherein at least one of the —$CH_2$— groups is substituted with —OH, —NHR', or —COOR', wherein R' represents H or C(1-8)alkyl,
$L_1'$ is a covalent bond or a straight-chain or branched C(1-6)alkyl, wherein one or more of the non-adjacent $CH_2$ groups may independently be replaced by a group selected from —O—, —CO—O—, —O—CO—, —NR'"—, —NR'"—CO—, and —CO—NR'",
R'" represents H or C(1-8)alkyl,
q is 0, 1, 2, 3 or 4,
$R_9$ is H or C(1-8)alkyl, and
$R_{10}$ and $R_{11}$ are, independently of each other: H, —OH, or —OC(1-8)alkyl.

2. The compound according to claim 1, wherein m is 2.

3. The compound according to claim 1, wherein q is 0.

4. A pharmaceutical composition comprising at least one compound according to claim 1 and a pharmaceutically acceptable carrier.

5. The compound according to claim 1, having one of the formulae VIIIa, VIIIb or VIIIc:

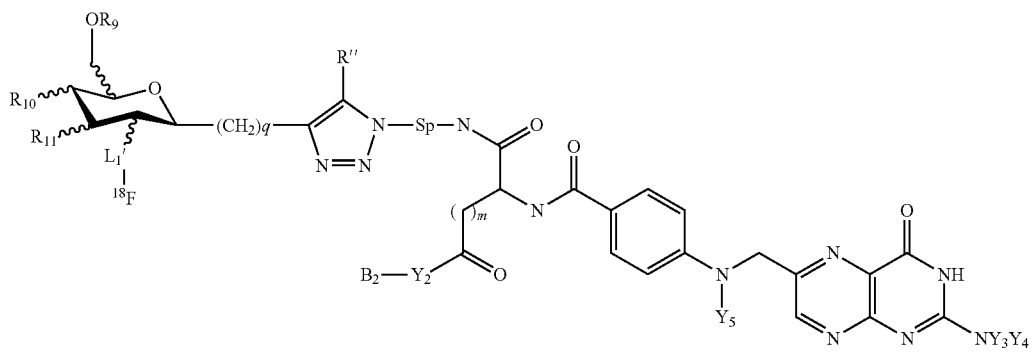

VIIIa

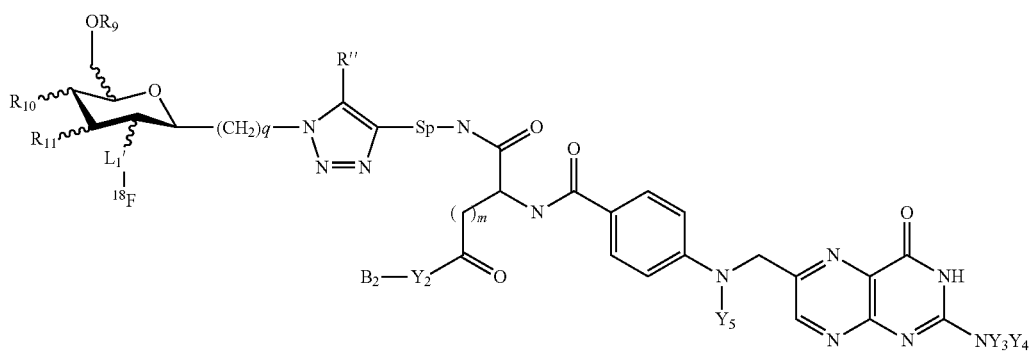

VIIIb

-continued

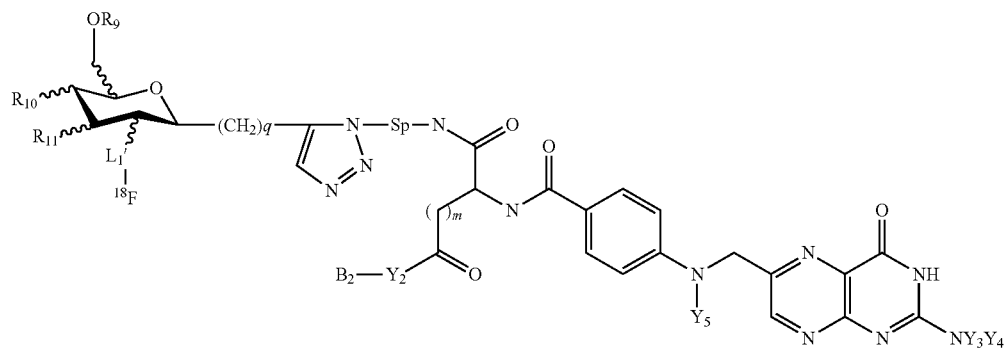

VIIIc wherein
$Y_3$ and $Y_4$ are, independently of each other: selected from H and C(1-4)alkyl, and
$Y_5$ is selected from H, C(1-4)alkyl or —COR', and
R' is H or C(1-4)alkyl.

6. The compound according to claim 1, which is of formula Va.

7. The compound according to claim 1, which is of formula Vb.

8. The compound according to claim 1, which is of formula Vc.

9. The compound according to claim 5, which is of formula VIIIa.

10. The compound according to claim 5, which is of formula VIIIb.

11. The compound according to claim 5, which is of formula VIIIc.

12. The compound according to claim 5, wherein m is 2.

13. The compound according to claim 5, wherein q is 0.

* * * * *